United States Patent
Ikeda et al.

(10) Patent No.: US 10,307,356 B2
(45) Date of Patent: Jun. 4, 2019

(54) METHOD FOR PRODUCING MYCOSPORINE-LIKE AMINO ACID USING MICROBES

(71) Applicants: THE KITASATO INSTITUTE, Minato-ku (JP); NAGASE & CO., LTD., Osaka-shi (JP)

(72) Inventors: Haruo Ikeda, Kawasaki (JP); Shogo Yamamoto, Kobe (JP); Jun Matsumoto, Kakogawa (JP); Masahiro Sota, Kobe (JP)

(73) Assignees: THE KITASATO INSTITUTE, Minato-ku (JP); NAGASE & CO., LTD., Osaka-shi (JP)

( * ) Notice: Subject to any disclaimer, the term of this patent is extended or adjusted under 35 U.S.C. 154(b) by 51 days.

(21) Appl. No.: 15/309,449

(22) PCT Filed: May 12, 2015

(86) PCT No.: PCT/JP2015/063682
§ 371 (c)(1),
(2) Date: Nov. 8, 2016

(87) PCT Pub. No.: WO2015/174427
PCT Pub. Date: Nov. 19, 2015

(65) Prior Publication Data
US 2017/0202762 A1 Jul. 20, 2017

(30) Foreign Application Priority Data
May 13, 2014 (JP) .................. 2014-099647

(51) Int. Cl.
| | |
|---|---|
| C12P 13/04 | (2006.01) |
| A61K 8/44 | (2006.01) |
| A61Q 17/04 | (2006.01) |
| A61Q 19/00 | (2006.01) |
| A61Q 19/08 | (2006.01) |
| A61K 8/99 | (2017.01) |
| A61K 31/198 | (2006.01) |
| C07C 249/14 | (2006.01) |
| C07C 251/20 | (2006.01) |
| C12N 15/09 | (2006.01) |
| C12R 1/465 | (2006.01) |
| A61K 35/00 | (2006.01) |
| A61K 36/00 | (2006.01) |

(52) U.S. Cl.
CPC ............... *A61K 8/44* (2013.01); *A61K 8/99* (2013.01); *A61K 31/198* (2013.01); *A61Q 17/04* (2013.01); *A61Q 19/00* (2013.01); *A61Q 19/08* (2013.01); *C07C 249/14* (2013.01); *C07C 251/20* (2013.01); *C12N 15/09* (2013.01); *C12P 13/04* (2013.01); *A61K 35/00* (2013.01); *A61K 36/00* (2013.01); *C07C 2601/16* (2017.05); *C12R 1/465* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 6,787,147 B1 | 9/2004 | Huner et al. | |
| 2010/0221812 A1* | 9/2010 | Bechthold | C12N 15/76 435/252.3 |
| 2014/0044653 A1* | 2/2014 | Qvit-Raz | C12N 15/746 424/59 |

FOREIGN PATENT DOCUMENTS

| | | |
|---|---|---|
| JP | 6-62878 A | 3/1994 |
| JP | 2009-120562 A | 6/2009 |
| JP | 2013-518871 A | 5/2013 |

(Continued)

OTHER PUBLICATIONS

Portwich et al., Ultraviolet and osmotic stresses induce and regulate the synthesis of mycosporines in the cyanobacterium Chlorogloeopsis PCC Arch. Microbiol. 172:187-192, 1999 (Year: 1999).*

(Continued)

*Primary Examiner* — David Steadman
(74) *Attorney, Agent, or Firm* — Oblon, McClelland, Maier & Neustadt, L.L.P.

(57) ABSTRACT

Provided are: a method for producing a mycrosporine-like amino acid (MAA) that includes a step in which microbes are cultivated that produce MAA on the outside of bacterial cells, a step in which the bacterial cells and extracellular culture fluid are separated, and a step in which the MAA is recovered from the extracellular culture fluid; an MAA indicated by formula (1), an MAA produced using this method, or an ultraviolet-absorbing composition including the MAA indicated by formula (1); and a composition including the MAA produced using this method or the MAA indicated by formula (1), for preventing at least one symptom or disease selected from a group comprising acute skin reactions, aging of the skin, and skin cancer.

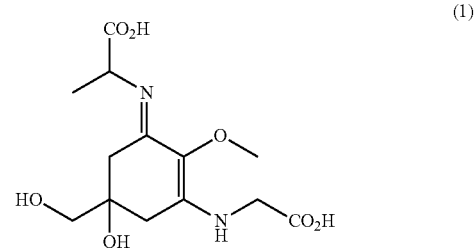

(1)

10 Claims, 2 Drawing Sheets
Specification includes a Sequence Listing.

(56) References Cited

FOREIGN PATENT DOCUMENTS

| JP | 2013-142058 A | 7/2013 | |
|---|---|---|---|
| WO | WO 02/39974 A1 | 5/2002 | |
| WO | WO-2010068413 A1 * | 6/2010 | ........... C07K 14/295 |
| WO | WO 2011/096628 A1 | 8/2011 | |

OTHER PUBLICATIONS

Bandaranayake, W. M., Nat. Prod. Rep. 15:159-172, 1998 (Year: 1998).*

Ehling-Schulz et al., "UV-B-Induced Synthesis of Photoprotective Pigments and Extracellular Polysaccharides in the Terrestrial Cyanobacterium Nostoc commune", J. Bacteriol. 179:1940-1945, 1997 (Year: 1997).*

Garcia-Pichel et al., "Evidence Regarding the UV Sunscreen Role of a Mycosporine-Like Compound in the Cyanobacterium *Gloeocapsa* sp.", Appl. Environ. Microbiol. 59:170-176, 1993 (Year: 1993).*

Prather et al., Curr. Opin. Biotechnol. 19:468-474, 2008 (Year: 2008).*

Kizer et al., Appl. Environ. Microbiol., 74:3229-3241, 2008 (Year: 2008).*

"Supporting Online Material", 2010, 49 pages; DOI: 10.1126/science. 1193637 (Year: 2010).*

Vernet et al., "Release of ultraviolet-absorbing compounds by the red-tide dinoflagellate *Lingulodinium polyedra*", Mar. Biol. 127:35-44, 1996 (Year: 1996).*

Extended European Search Report dated Jan. 23, 2018 in European Patent Application No. 15792252.7, 9 pages.

Emily P. Balskus, et al. "The Genetic and Molecular Basis for Sunscreen Biosynthesis in Cyanobacteria", Science, XP-055083282, vol. 329, No. 5999, Sep. 24, 2010, pp. 1653-1656.

Fernando Colabella, et al. "UV Sunscreens of Microbial Origin: Mycosporines and Mycospo-rine-like Aminoacids", Recent Patents on Biotechnology, XP-002776894, vol. 8, No. 3, 2014, pp. 179-193.

International Search Report dated Jul. 14, 2015 in PCT/JP2015/063682 (submitting English translation only, previously filed).

International Preliminary Report on Patentability and Written Opinion dated Nov. 24, 2016 in PCT/JP2015/063682 (submitting English translation only).

Office Action dated Nov. 10, 2015 in Japanese Patent Application No. 2015-545234 (with English translation).

Rungaroon Waditee-Sirisattha, et al., "Identification and Upregulation of Biosynthetic Genes Required for Accumulation of Mycosporine-2-Glycine under Salt Stress Conditions in the Halotolerant Cyanobacterium *Aphanothece halophytica*", Applied and Environmental Microbiology, vol. 80, No. 5, 2014, pp. 1763-1769.

Qunjie Gao, et al., "An ATP-Grasp Ligase Involved in the Last Biosynthetic Step of the Iminomycosporine Shinorine in *Nostoc punctiforme* ATCC 29133", Journal of Bacteriology, vol. 193, No. 21, 2011, pp. 5923-5928.

Kiyoko T. Miyamoto, et al., "Discovery of Gene Cluster for Mycosporine-Like Amino Acid Biosynthesis from *Actinomycetales* Microorganisms and Production of a Novel Mycosporine-Like Amino Acid by Heterologous Expression", Applied and Environmental Microbiology, vol. 80, No. 16, 2014, pp. 5028-5036.

Shailendra P. Singh, et al., "Role of various growth media on shinorine (mycosporine-like amino acid) concentration and photosynthetic yield in *Anabaena variabilis* PCC 7937", World J. Microbiol Biotechnol, 24, 2008, pp. 3111-3115.

D. Karentz, et al., "Survey of mycosporine-like amino acid compounds in Antarctic marine organisms: potential protection from ultraviolet exposure", Marine Biology, 108, 1991, pp. 157-166.

Kazuo Yabe, "Purification and Crystallization of UV-absorbing compounds: Mycosporine-like amino acids—Palythine, Shinorine and Porphyra-334—from Marine red algae.", Photomedicine and Photobiology, vol. 24, 2002, pp. 39-42.

Francesco Chioccara, "Occurrence of two new mycosporine-like aminoacids, mytilins a and b in the edible mussel, mytilus galloprovincialis", Tetrahedron Letters, No. 34, 1979, pp. 3181-3182.

Diego Libkind, et al., "Production of the UVB-absorbing compound mycosporine-glutaminol-glucoside by *Xanthophyllomyces dendrorhous* (*Phaffia rhodozyma*)", FEMS Yeast Res, 11, 2011, pp. 52-59.

* cited by examiner

```
                       SEQUENCE LISTING

<160> NUMBER OF SEQ ID NOS: 15

<210> SEQ ID NO 1
<211> LENGTH: 1020
<212> TYPE: DNA
<213> ORGANISM: Actinosynnema mirum DSM 43827

<400> SEQUENCE: 1
gtgcttcgtg ttctgcacct gaccggttcg ccggtgagcc cgttcttcgc cgaactgtcc      60
actgtgtacg gtcggggctg cctgggcgcg gcggcggacc cggcgcgcta cgagttcctg     120
gtggcgcacg tgaccccgga cggccgctgg cgcttcccgg cggacctgac gccggaggcg     180
ctggcggctg cacccaggct ggggctgccc gaggcgctgg gcctgatcga atcccggtcg     240
gtggacgtgg ccgtgccgca gctgttctgc ccgcccggca tgaccacgta ccgcgcgctg     300
ctggacgccc tgggcgtgcc gtaccccgga aacccgccgg acgtgatggc gctgggcgcg     360
gacaaggcga tgacccgcgc ggtcgtggcg gcggcgggcg tccccgtccc ggagggccgc     420
gtggtcacct cggccgaccc ctgcccgctc ccgccgcgcgt tcgtggtgaa gcccgtggac     480
gccgacaact ccgacggcct gaccctggtg cacgaccgcg ccgactacca cgcggccctg     540
gacgcggcgt tcgctgctc gccccgccgc agggccttgg tggagcgcta cgtgccaccg     600
ggccgcgagg tccgctgcgg cgtgctcgtc agatccggcg tcccgacgcc gctcccctgt     660
gaggagtacc cgctcccgtc cggcgtccgc ccccgcgcgg acaagctggc cgacgacggg     720
ggcggctccc tgtccctggt ggccaaggcg gacgccgct cgtggatcgt cgaccacgac     780
```

```
gacccggtga cggcggccgt gcaggagcag gcgctgcgct gccacgaggc gctgggctgc    840
cgcgactaca gcctgttcga cttccggatc gacccggagg ggcggccgtg gttcctggag    900
gcggggttgt actgctcgtt cgcgccgacg agcgtgatca cgacgatggc gggcgcggcg    960
gggatcgggt tggcggagct gttcgccgag gccgtcacca ccgccgcgcg caggggggtga  1020
```

<210> SEQ ID NO 2
<211> LENGTH: 1290
<212> TYPE: DNA
<213> ORGANISM: Actinosynnema mirum DSM 43827

<400> SEQUENCE: 2

```
gtgtcccgga ccctgggcgc gctcgcgctg ctcctcgcgg ccctgccgtt cagcgccgcc     60
ctcaccgccg tggcggcgct gcgcgcggcg gtccggccat cgcccgcgcg ggcgacgccg    120
aggcggccga ggacggtgct gctgaccggc ggcaagatga ccaaggcgct gcacctggcg    180
cgcgcgttcc accgggccgg gcaccgggtc gtgctggtgg agacggcccg ctaccggctg    240
accgcgcacc ggttctcccg cgcggtcgac gcgttccacg tcgtgccgga ctcggccgac    300
ccccgctacc cgcaggcgct cctcgcgatc gtggagcggg agggcgtgga cgtgttcgtg    360
ccggtgtgca gcccggcgtc cagcgtccac gacgccgccg ccgcgccgct gctggcgacc    420
cggtgcgagg tgctgcacgc cgggctggag gtggtggagc tgctggacga caagcaccgc    480
ttcgccgagc tgtccgccga gctgggcctc ccggttcccc gctcgcaccg gatcaccgcg    540
ccggagcagg tgctcgacct ggggctggac gggccgcacg tgctcaagag catcccgtac    600
gacccggtga accggctgga cctgaccccg ctgccgaggc cgactcccga ggcgacgctg    660
gagttcctgc gcggcaagga cgtccgggac gggcacccgt gggtgctgca ggagttcgtg    720
gcgggcaagg agtactgcac gcacagcacc gtccggaacg gccgggtggt ggtctacggg    780
tgctgcgagt cctcggcgtt ccaggtgaac tacgagatgg tggacaagcc ggagatcgag    840
cgctgggtgc gggccttcgc cgaggccacc ggggtgaccg gcaggtgtc gttcgacttc    900 atcgagtcgg cggacggccg cgcgctcgcc atcgagtgca acccgcgcac ccacagcgcc    960
atcaccatgt ccacgacca cccggacctg gccgcgcct acctggaccc ggacgcgccg   1020
cagatccggc cgctgccgtc gagcaggccg acgtactggc tgttccacga gctgtggcgg   1080
gccctgtccg aaccggggac cgcgcgggag cggctgcggg tggtggcgcg cggcaaggag   1140
gcggtcttcg actggtccga cccgctgccg ttcctgctgc tgcaccacgt gcacgtgccg   1200
ctgctgctgc tgcgggcgct ggtgcgcggg caggactggg tgcgggtgga cttcaacatc   1260
ggcaagctgg tggcgccctc gggggactga                                    1290
```

<210> SEQ ID NO 3
<211> LENGTH: 855
<212> TYPE: DNA
<213> ORGANISM: Actinosynnema mirum DSM 43827

<400> SEQUENCE: 3

```
gtgaacccgt tgcccaccaa gggctccgcg tccggcgccg tgtccgcgcc gggcgcgccc     60
cgcccggtga cgccggtggc gctgctggcc gacaccctgg cccggttggc ggggcggtcg    120
gacctgccgc ccgacgtcgt cgccgagctg tccgccgccc cgagctggc gtccggagtg    180 gacggttacg ccggtcggtg caccacgccg gagtcgcccg cgctgcgcga gctggccgcc    240
aggaccgccg agcacgactg gcggggacgg ggcggcgggg tcgcgctgga gcaggagatg    300
ctgtccgggc acgtcgaggg gcagctgctc aagaccctgc tgcgggcgct gcggggcgcgg   360
```

| | |
|---|---|
| cgggtgctgg agatcggcat gttcaccggc tactcggcgc tcgccatggc cgaggagctg | 420 |
| ccggacgacg gggtcgtcgt cgcctgcgag ctggacccgg acgtggcggc cttcgcccgc | 480 |
| gagcggttct ccgcctcgcc gcacggccgg aaggtcgacg tgcgggtcgg gcccgcgctg | 540 |
| gacaccctgg cgggattggt gggcggcgag ccgttcgacc tggtgttcgt ggacgcggac | 600 |
| aaggccgggt acaccgagta cctcgcggtc gtgctggacg gcgggctgct cgcgccgcac | 660 |
| gggctggtgt gcgtggacaa cacgctgatg cagggcaaga cctacctgcc cggcgcccgt | 720 |
| gacgcggtgg gcgcggccgt ggaccggttc aaccggcacg tggcgcagcg gccggacgtg | 780 |
| gcgcaggtgc tcgtgccggt gcgcgacggg ctcaccctga ccgcagggt gacgcccgga | 840 |
| acgggggagc cgtga | 855 |

<210> SEQ ID NO 4
<211> LENGTH: 1221
<212> TYPE: DNA
<213> ORGANISM: Actinosynnema mirum DSM 43827

<400> SEQUENCE: 4

| | |
|---|---|
| atgacgacga acctcaccgc gacggtcacc gccacggaga cgacttccg ggtgcgcgcc | 60 |
| gtcgaggagc gcgactacct gctgacctac gtggacgggg cgttctcccc ggagagcagc | 120 |
| cggatcgccg accaccaccg cgcgcacggc cggtgcctga tgatcgtcga cgccaacgtc | 180 |
| caccgcctgc acggcgaccg catccggggcc tacttcgagc accacggcat cgcgctcacc | 240 |
| gcgctcccgc tggccatcga cgagacgcag aagtcgctgc gcacagtcga gcggatcgtg | 300 |
| gacgccttcg gcgagttcgg gctgatccgc aaggagcccg tgctcgtggt cggcggcggc | 360 |
| ctgctgaccg acgtggccgg gttcgcgtgc gcggtgttcc gccgctccac cgactacgtg | 420 |
| cgggtgccca cctcgctgat cgggctcatc gacgccagcg tcgcgatcaa ggtcgcggtg | 480 |
| aaccacggcc gcaccaagaa ccggctgggg cgttccacg cgtccaagga ggtcgtgctc | 540 |
| gacttctcgt tcctggggac gctgccgacc gagcaggtcc gcaacggcat ggccgagctg | 600 |
| gtcaagatcg ccgtggtggc gaacgcggag gtgttccggc tgctggagaa gtacggcgag | 660 |
| gacctgctgc acaccgcgtt cggcacggtc gacggcaccc cgcagctgcg cgagaccgcc | 720 |
| cgcaaggtca cccacgaggc catcggcacc atgctggcgc tggaggcgcc gaacctgcgg | 780 |
| gagctggacc tggaccgggc gatcgcgttc ggccacacct ggagcccgc gctggagctg | 840 |
| gccccggaaa ccccctacct gcacgggcac gcgatcagcg tcgacatggc gctgtcctgc | 900 |
| acgatcgccg agcggcgcgg ctacctggcg accagcgagc gcgaccggat cttctggctg | 960 |
| ctgagcaagg tcggcctgtc gctggacagc ccgcacctga cgccggagct gctgcgcgcg | 1020 |
| gccaccgagt cgatcgtgca gacccgcgac gggctccagc gcgccgcgat gccccggccg | 1080 |
| atcgggacgt gctgcttcgt caacgacctc accgagtccg agctgctgga cgggctcgcc | 1140 |
| gcgcaccgcg agctggtcgc ccgctacccc aggggcggcg cgggcgagga cgtgcgggtc | 1200 |
| accaggagcg gtgccgcgtg a | 1221 |

<210> SEQ ID NO 5
<211> LENGTH: 1041
<212> TYPE: DNA
<213> ORGANISM: Pseudonocardia sp. P1

<400> SEQUENCE: 5

| | |
|---|---|
| tcaccggtgg tccgacgatg tctgcctgac ctcctgtcgg gcggcagaga tcagatcagc | 60 |

-continued

```
gaacagctct cgtaccggtg ttgcggcggc gtgggccatc gtcgcgacga ccgaggagtg      120
ggcgaacgag cagtacaggc cggcctcgag gaagtagagg cggccgttcg ggtcgactcg      180
gaagtcgaag agcccatagt ggcggcatcc caacgcccgg taggcgcgcc gagcggcgtc      240
gtgaactgtc gcggtgagcg gatcggcggg atcgacgatc caggaccggt catccttggc      300
gaccaaacgc aggtcgccgg tggcagagcg gtcgagcttg tcgtcggcga gtcggatcgg      360
cttgtctgtc gggtccatgc ggtactcctc gaggggcagg cctacgaggt caccgccgcg      420
atcgatgatg ccgcaccgta cttcccggcc gagaggtacg aactgttcga ccagcgctcg      480
ctcactgtgg gcaagagcgt cttttgatcgc cacctcgatg gtctcgtcgg tctcggccaa      540
ggtcacgccg accgagttgt cggtgtcgac aggtttgatc acgagcggtg gccggagggt      600
gggggcttgt cctgcgcgga gtacctctcc ggccggaacc gcgacaccgg cgtgtgcgac      660
gacggcgcgg gcgcgggcct tgtccgctcc gagcgccatc acgtccgggg tgttgcccac      720
gtaggggatc ccttgcagat cgaacagcgc ccggtagtgg gtcatgccgg tcggcagaa       780 catctggggc accatcacgt cgatcttgag acgtgcgatg tgggcgaggg cctcgggtag      840
cgacagcagc ggggcggcgg cgatgtcgcc gggcgccagg cctacgggga actgccaccc      900
acccggtgtc acgtaggcga tgtggacgtc gtagcgggtg gggtcggcgg tggcggtgag      960
gcagtctgcg gcgtagaggc gggacaggtc gcagaagaac tcgtcgaccg gcgatccggt     1020
caggtgcagc accgtgatca t                                               1041

<210> SEQ ID NO 6
<211> LENGTH: 1236
<212> TYPE: DNA
<213> ORGANISM: Pseudonocardia sp. P1

<400> SEQUENCE: 6
tcagtccccc gcggattcga cgagcttgcc gatgttgatg tcgatcttta cccagggcgt       60
gccacgtacc agcttgtcga gcagcagcgc ggcgatctgc aggtgaggga ccagcaggaa      120
cggcagcggg tcccgcgctt cgagcagtgc ttccttgccg cggaggatgg tgcgtaaccg      180
cttgggcagc gacgtcggag ccccgaggag ccggccgagc tcgtggtaga gccagtaggt      240
cgggcgggca cccgggtcgg ggaccgccgg tgggccggcg tgggccgaga ggtaggcgtc      300
agcgagacct gggtggtcgt ggaacagggt gatcgctgag tgggtacgtg gattgcactc      360
gatcgcgtac acgctgccgt cggcgcgttc gatgaagtcg aacgacagct gcccggtgac      420
gccgagttcg gtgcagaacc ggcggaccca ttcgtcgatg acggggtggg tgactgcggt      480
gtagttgagc tggaaggccg aggaggggca gcagcagtgc agtgccacgg cgccgtcgcg      540
gacggtggag tgtgtgcagt actcggtgcc ctccacgaac tcctgcagta tccagggggtt     600 gtccgacgag atcggtagcc ggcgtacgaa gtcggctgtc tggtgggcgg tcgggtgcgg      660
tagacgggtg aggtccatgc gtcggaccgg gtcgtaggcg atcgatttca ggacgtaggt      720
gcttccgggc gcgaggtga agtcgaagtc gatgacttgt tgcgggtcgg tgatcctgtg      780
ggtgtccggc accggcaggc ccatggctgc ggcggcctgg gcgaaacggt gtttgtcgtc      840
gagcagcgct acgacgtcgc tgtccaggtg cacgacctcg cagagtggct cgagcgcttg      900
cttggcgtcg gcgtcgtacc agctggcgag ggggctgcac accggaacgt agacgtcgac      960
gccctcgtgc tgggcgatct cggcgagtcg ttcggcgtag tcgggcgcgt cgggtgcagg     1020
gacgacgtgg aaggcgtcga cggctcggga gaagcggtgc ccgacagtc ggtagcgggc      1080 ctgctccacg agcacgaccc ggtgcccggc gtcatgaaac gcacgggcca gtgtgagcgc     1140
```

```
tttggtcatc ttcccgcccg acagcatgat cgtctgtcgg gtggctgtgc tgcgcgggcg    1200
gcgtgcccgc cgggtcagcc cgatcagcgc ggccat                              1236

<210> SEQ ID NO 7
<211> LENGTH: 753
<212> TYPE: DNA
<213> ORGANISM: Pseudonocardia sp. P1

<400> SEQUENCE: 7
tcacgacgcc caccggatca gggtcagtcc gtctcggagc gggacgagga cctgttcgat      60
acgcggatca tcggtgacgg atctgttgaa cgccgcgatc gccgtgccgt tcggggtgga    120
ctcgcccgtc cagggctgcc cctgcatcaa ggtgttgtcg acacacatca ccccgtgcgg    180
ggcgagcagg ccgccttgca gcacggcgtc gaggtattcg gcgtatccgc ccttgtcggc    240
gtcgaggaag atcaggtcga agcgctgtcc gaccagtgtg gcgagggtgt cggtggccgc    300
gccgacttcg atcgtgatgc gctgggaggc cgtggaccgg agagagcttc acgcgcgag    360 tgctgccgcg tgcgggtcga tctcgcaggc gatcaactca ccgtcctcgg gtagcgcttc    420
ggccatggcc agggccgagt agccggtgaa catcccgatc tcgagtaccc gtttggcctg    480
catggcctgg accaggaaac gcaggaagcg ccctcgacg tgtccggaga gcatctcttg    540
ctcgaggccg cttgcggtgt ggtcccagtt ctcggcgctg gtccggcgtt ccagttcccc    600
cagcgcgtgg gacgccggcg aggtgtgctc gtcgaggtag ggatccaggc cggaggcgag    660
gtcgcgggca cgaagcaggt ccggttcgac gtcgggcccg gccgggcga ccaggtcgtc    720 gagcagaccg gccaggatcg tcgtcggcgt cac                                 753

<210> SEQ ID NO 8
<211> LENGTH: 1230
<212> TYPE: DNA
<213> ORGANISM: Pseudonocardia sp. P1

<400> SEQUENCE: 8
tcatgtcctg gcctcggtgt tcggggcggt cgtcaactct gtcttcgccg acgaccacat     60
ctcgacacct tctaccgatg tcggtaggcc agcgacgacg gccttgtgtg cggcaagggt    120
ttcgatcagt tccgtgtgct cgatgtcgtt ggcgaagtga cacgttccga tcgggcgggg    180
cagggcggcg cgtagcttcc ccgctcgtgt ctgcatgatc gatgcggtcg catcgatgag    240
cagctgctcg gtgaggtagg tgctgtcgac actgagtccg agtccgctga acagtcggtg    300
gatgcggtcg cgctccccgg tggtgatgtc gccgcgcgc gcggccaggg tcgccgagaa    360
cgccatgtcg atggcgatcg cgtgaccgtg caacatcggc gtgggtgggg cgagctccag    420
ggtcgggctc catgtgtggc cgaacgcgat gacgcgatcc aggtcgagtt cgtgcaggtt    480
gcggtgctcg agttcgagca tggtgtggat ggcgtcgtag gtgcaccggt gggcgatctg    540
gcgcagttcc ggggtgccct cgcggtgccc gaagcgtgtg gcgagcaggt cgtcgccgta    600
tttctccagc aggtcgaaca ggccggcgtt cgccacggtc gcaatcttga tcatctcggc    660
gacgccgttg cggacctgcg cttcgggcaa ggtggccagg aacgagaagt cgagcaggac    720
ctgttgcgag gcgtggaagg cgccgagacg attcttgtgt ctgccgtggt tgaccgcgac    780
cttcatcgcg acactcgcgt cgatgagacc gatcagcgtg gtgggatcc tgacgtaggg    840 cgtgccacgc ttgtagctgg cgcaggcgaa cccggtgacg tcgtggtca agcctccacc    900 gacgacgagc accggttcgg tgcgcagtag cccgaagtcg gcgtaggcgt cgacgatgcg    960
```

```
ctcgagagtg cgcaggctct tggccgtctc ggcgatggtc agtggtacga gggtcacggc   1020
gatgtcgtgg tggtcgaaat agctgcggat cgggtcgccg tagtgttcgt ggacggtctc   1080
gtcgatcacc atcaggcacc ggccccatgg ccgatagagg tcggcgagct cggtgttgtg   1140
gggcgcgaac acgccgtcga cgtaggagag cgtgaactcg atccgctccc aactctcgac   1200
acggaactcc gtatcggtcg cgctgagcac                                    1230
```

<210> SEQ ID NO 9
<211> LENGTH: 1020
<212> TYPE: DNA
<213> ORGANISM: Artificial Sequence
<220> FEATURE:
<223> OTHER INFORMATION: Codon-optimized amir_4256 for SAM2179

<400> SEQUENCE: 9

```
atgctccgcg tgctccacct caccggtagc cctgtgagcc ccttctttgc cgagctcagc     60
accgtgtacg gccgcggctg cctcggtgcc gccgccgatc ctgcccgcta cgagtttctc    120
gtggcccacg tgaccccccga cggtcgctgg cgcttccctg ccgatctcac ccctgaggcc   180
ctcgccgccg cccctcgcct cggcctcccc gaggccctcg gtctcattga gccgcagc     240 gtggacgtgg ccgtgcccca gctcttctgc cctcccggta tgaccaccta ccgcgccctc    300
ctcgatgccc tcggcgtgcc ctaccctggt aaccctcccg acgtgatggc cctcggcgcc    360
gacaaggcca tgacccgcgc cgtggtggcc gccgccggtg tgcccgtgcc cgagggtcgc    420
gtggtgacca cgccgatcc ctgccctctc cctcctccct ttgtggtgaa gccgtggat     480 gccgacaaca gcgatggcct caccctcgtg cacgatcgcg ccgactacca cgccgccctc    540
gacgccgcct ttgcctgcag ccctcgccgc gcgccctcg tggagcgcta cgtgcctccc    600
ggtcgcgagg tgcgctgcgg cgtgctcgtg cgcagcggtg tgcccacccc tctcccctctc   660 gaggagtacc ctctccccag cggtgtgcgc ccccgcgccg acaagctcgc cgatgatggc    720
ggtggcagcc tcagcctcgt ggccaaggcc gacggtcgca gctggattgt ggaccacgat    780
gatcccgtga ccgccgccgt gcaggagcag gccctccgct gccacgaggc cctcggctgc    840
cgcgactaca gcctcttcga cttccgcatt gatcccgagg tcgcccctg gtttctcgag    900 gccggcctct actgcagctt tgcccctacc agcgtgatca ccaccatggc cggtgccgcc    960
ggcatcggtc tcgccgagct cttcgccgag gccgtgacca ccgccgcccg ccgcggttga  1020
```

<210> SEQ ID NO 10
<211> LENGTH: 1290
<212> TYPE: DNA
<213> ORGANISM: Artificial Sequence
<220> FEATURE:
<223> OTHER INFORMATION: Codon-optimized amir_4257 for SAM2179

<400> SEQUENCE: 10

```
atgagccgca ccctcggtgc cctcgccctc ctcctcgccg ccctcccttt cagcgccgcc     60
ctcaccgccg tggccgccct ccgcgccgcc gtgcgcccca gccccgcccg cgccacccct    120 cgccgcccctc gcaccgtgct cctcaccggt ggcaagatga ccaaggccct ccacctcgcc   180
cgcgcctttc accgcgccgg ccaccgcgtg gtgctcgtgg agaccgcccg ctaccgcctc    240 accgccacc gcttcagccg cgccgtggat gcctttcacg tggtgcccga cagcgccgat    300
cctcgctacc tcaggccct cctccgccatt gtggagcgcg agggtgtgga tgtgttcgtg    360
cccgtgtgca gccccgccag cagcgtgcac gatgccgccg ccgcccctct cctgccacc    420 cgctgcgagg tgctccacgc cggcctcgag gtggtggagc tcctcgacga taagcaccgc    480
```

```
tttgccgagc tcagcgccga gctcggtctc cccgtgcctc gcagccaccg catcaccgcc      540
cctgagcagg tgctcgatct cggcctcgac ggtccccacg tgctcaagag cattccctac      600
gatcccgtga accgcctcga cctcacccct ctccctcgcc ccaccccctga ggccacccctc    660 gagttcctcc gcggcaagga tgtgcgcgac ggtcacccct gggtgctcca ggagttcgtg      720
gccggcaagg agtactgcac ccacagcacc gtgcgcaacg tcgcgtggt ggtgtacggc       780 tgctgcgaga gcagcgcctt tcaggtgaac tacgagatgg tggataagcc cgagatcgag      840
cgctgggtgc gcgcctttgc cgaggccacc ggcgtgaccg gtcaggtgag cttcgacttt      900
attgagagcg ccgacggtcg cgccctcgcc atcgagtgca accctcgcac ccacagcgcc      960
attaccatgt ccacgatca ccccgacctc gcccgcgcct acctcgaccc cgatgcccct     1020
cagattcgcc ctctccctag cagccgcccc acctactggc tctttcacga gctctggcgc     1080
gccctcagcg agcctggcac cgcccgcgag cgcctccgcg tggtggcccg cggtaaggag     1140
gccgtgttcg actggagcga tcccctcccc tttctcctcc tccaccacgt gcacgtgccc     1200
ctcctcctcc tccgcgcccct cgtgcgcggt caggattggg tgcgcgtgga ctttaacatc     1260
ggcaagctcg tggcccctag cggcgactga                                       1290
```

<210> SEQ ID NO 11
<211> LENGTH: 855
<212> TYPE: DNA
<213> ORGANISM: Artificial Sequence
<220> FEATURE:
<223> OTHER INFORMATION: Codon-optimized amir_4258 for SAM2179

<400> SEQUENCE: 11

```
atgaaccctc tccccaccaa gggtagcgcc agcggcgccg tgagcgcccc tggtgcccct       60
cgccccgtga cccctgtggc cctcctcgcc gataccctcg cccgcctcgc cggtcgcagc      120
gacctcccct ctgatgtggt ggccgagctc agccgccgcg ccgagctcgc cagcggcgtg      180
gacggctacg ccggtcgctg caccacccct gagagccccg ccctccgcga gctcgccgcc      240
cgcaccgccg agcacgattg gcgcggtcgc ggcggtggcg tggcccctcga gcaggagatg     300 ctcagcggcc acgtggaggg tcagctcctc aagaccctcc tccgcgccct ccgcgcccgc     360
cgcgtgctcg agattggcat gttcaccggt tacagcgccc tcgccatggc cgaggagctc      420
cccgacgatg gtgtggtggt ggcctgcgag ctcgatcccg atgtggccgc cttgccccgc      480
gagcgcttca gcgccagccc tcacggtcgc aaggtggacg tgcgcgtggg tcccgccctc      540
gacaccctcg ccggcctcgt gggtggcgag ccttttgatc tcgtgttcgt ggatgccgac     600
aaggccggct acaccgagta cctcgccgtg tgctcgacg gcggtctcct cgcccctcac      660
ggcctcgtgt gcgtggacaa caccctcatg cagggcaaga cctacctccc cggtgcccgc     720
gatgccgtgg gtgccgccgt ggatcgcttt aaccgccacg tggcccagcg ccccgacgtg     780
gcccaggtgc tcgtgcccgt gcgcgacggc ctcaccctca tccgccgcgt gaccctggc      840 accggtgagc cctga                                                       855
```

<210> SEQ ID NO 12
<211> LENGTH: 1221
<212> TYPE: DNA
<213> ORGANISM: Artificial Sequence
<220> FEATURE:
<223> OTHER INFORMATION: Codon-optimized amir_4259 for SAM2179

<400> SEQUENCE: 12

| | |
|---|---:|
| atgaccacca acctcaccgc caccgtgacc gccaccgaga cgactttcg cgtgcgcgcc | 60 |
| gtggaggagc gcgattacct cctcacctac gtggacggtg ccttcagccc tgagagcagc | 120 |
| cgcattgccg atcaccaccg cgcccacggt cgctgcctca tgatcgtgga cgccaacgtg | 180 |
| caccgcctcc acgcgatcg cattcgcgcc tacttcgagc accacggcat cgccctcacc | 240 |
| gccctccctc tcgccatcga cgagacccag aagagcctcc gcaccgtgga gcgcatcgtg | 300 |
| gatgcctttg gcgagtttgg tctcattcgc aaggagcccg tgctcgtggt gggcggtggc | 360 |
| ctcctcaccg acgtggccgg tttcgcctgc gccgtgtttc gccgcagcac cgattacgtg | 420 |
| cgcgtgccca ccagcctcat ggcctcatt gatgccagcg tggccatcaa ggtggccgtg | 480 |
| aaccacggtc gcaccaagaa ccgcctcggt gcctttcacg ccagcaagga ggtggtgctc | 540 |
| gacttcagct ttctcggcac cctccccacc gagcaggtgc gcaacggcat ggccgagctc | 600 |
| gtgaagattg ccgtggtggc caacgccgag gtgttccgcc tcctcgagaa gtacggtgag | 660 |
| gatctcctcc acaccgcctt tggcaccgtg gatggtaccc ctcagctccg cgagaccgcc | 720 |
| cgcaaggtga cccacgaggc cattggcacc atgctcgccc tcgaggcccc taacctccgc | 780 |
| gagctcgacc tcgatcgcgc cattgccttc ggtcacacct ggagccccgc cctcgagctc | 840 |
| gcccctgaga cccctacct ccacggccac gccatcagcg tggacatggc cctcagctgc | 900 |
| accattgccg agcgccgcgg ttacctcgcc accagcgagc gcgatcgcat cttttggctc | 960 |
| ctcagcaagg tgggcctcag cctcgacagc ccccacctca cccctgagct cctccgcgcg | 1020 |
| gccaccgaga gcatcgtgca gacccgcgat ggtctccagc gcgccgccat gcctcgcccc | 1080 |
| attggcacct gctgcttcgt gaacgacctc accgagagcg agctcctcga tggtctcgcc | 1140 |
| gcccaccgcg agctcgtggc ccgctaccct cgcggtggcg ccggcgagga cgtgcgcgtg | 1200 |
| acccgcagcg gtgccgcctg a | 1221 |

<210> SEQ ID NO 13
<211> LENGTH: 957
<212> TYPE: DNA
<213> ORGANISM: Scheffersomyces stipitis

<400> SEQUENCE: 13

| | |
|---|---:|
| atgccttcta ttaagttgaa ctctggttac gacatgccag ccgtcggttt cggctgttgg | 60 |
| aaagtcgacg tcgacacctg ttctgaacag atctaccgtg ctatcaagac cggttacaga | 120 |
| ttgttcgacg gtgccgaaga ttacgccaac gaaaagttag ttggtgccgg tgtcaagaag | 180 |
| gccattgaca aggtatcgt caagcgtgaa gacttgttcc ttacctccaa gttgtggaac | 240 |
| aactaccacc acccagacaa cgtcgaaaag gccttgaaca gaaccctttc tgacttgcaa | 300 |
| gttgactacg ttgacttgtt cttgatccac ttcccagtca ccttcaagtt cgttccatta | 360 |
| gaagaaaagt acccaccagg attctactgt ggtaagggtg acaacttcga ctacgaagat | 420 |
| gttccaattt tagagacctg gaaggctctt gaaaagttgg tcaaggccgg taagatcaga | 480 |
| tctatcggtg tttctaactt cccaggtgct ttgctcttgg acttgttgag aggtgctacc | 540 |
| atcaagccat ctgtcttgca agttgaacac caccatact tgcaacaacc aagattgatc | 600 |
| gaattcgctc aatcccgtgg tattgctgtc accgcttact cttcgttcgg tcctcaatct | 660 |
| ttcgttgaat tgaaccaagg tagagctttg aacacttctc cattgttcga aacgaaact | 720 |
| atcaaggcta tcgctgctaa gcacggtaag tctccagctc aagtcttgtt gagatggtct | 780 |
| tcccaaagag gcattgccat cattccaaag tccaacactg tcccaagatt gttgaaaaac | 840 |
| aaggacgtca acagcttcga cttggacgaa caagatttcg ctgacattgc caagttggac | 900 |

```
atcaacttga gattcaacga cccatgggac tgggacaaga ttcctatctt cgtctaa      957
```

<210> SEQ ID NO 14
<211> LENGTH: 1092
<212> TYPE: DNA
<213> ORGANISM: Scheffersomyces stipitis

<400> SEQUENCE: 14

```
atgactgcta acccttcctt ggtgttgaac aagatcgacg acatttcgtt cgaaacttac    60
gatgccccag aaatctctga acctaccgat gtcctcgtcc aggtcaagaa aaccggtatc   120
tgtggttccg acatccactt ctacgcccat ggtagaatcg gtaacttcgt tttgaccaag   180
ccaatggtct tgggtcacga atccgccggt actgttgtcc aggttggtaa gggtgtcacc   240
tctcttaagg ttggtgacaa cgtcgctatc gaaccaggta ttccatccag attctccgac   300
gaatacaaga gcggtcacta caacttgtgt cctcacatgg ccttcgccgc tactcctaac   360
tccaaggaag gcgaaccaaa cccaccaggt accttatgta agtacttcaa gtcgccagaa   420
gacttcttgg tcaagttgcc agaccacgtc agcttggaac tcggtgctct tgttgagcca   480
ttgtctgttg gtgtccacgc ctctaagttg ggttccgttg ctttcggcga ctacgttgcc   540
gtctttggtg ctggtcctgt tggtcttttg gctgctgctg tcgccaagac cttcggtgct   600
aagggtgtca tcgtcgttga catttttcgac aacaagttga agatggccaa ggacattggt   660
gctgctactc acaccttcaa ctccaagacc ggtggttctg aagaattgat caaggctttc   720
ggtggtaacg tgccaaacgt cgttttggaa tgtactggtg ctgaaccttg tatcaagttg   780
ggtgttgacg ccattgcccc aggtggtcgt ttcgttcaag tcggtaacgc tgctggtcca   840
gtcagcttcc caatcaccgt tttcgccatg aaggaattga ctttgttcgg ttcttttcaga   900
tacggattca acgactacaa gactgctgtt ggaatctttg cactaactaa ccaaaacggt   960
agagaaaatg ctccaattga ctttgaacaa ttgatcaccc acagatacaa gttcaaggac  1020
gctattgaag cctacgactt ggtcagagcc ggtaagggtg ctgtcaagtg tctcattgac  1080
ggccctgagt aa                                                      1092
```

<210> SEQ ID NO 15
<211> LENGTH: 1803
<212> TYPE: DNA
<213> ORGANISM: Saccharomyces cerevisiae

<400> SEQUENCE: 15

```
atgttgtgtt cagtaattca gagacagaca agagaggttt ccaacacaat gtctttagac    60
tcatactatc ttgggtttga tctttcgacc caacaactga aatgtctcgc cattaaccag   120
gacctaaaaa ttgtccattc agaaacagtg gaatttgaaa aggatcttcc gcattatcac   180
acaaagaagg gtgtctatat acacggcgac actatcgaat gtccegtage catgtggtta   240
gaggctctag atctggttct ctcgaaatat cgcgaggcta aatttccatt gaacaaagtt   300
atggccgtct cagggtcctg ccagcagcac gggtctgtct actggtcctc ccaagccgaa   360
tctctgttag agcaattgaa taagaaaccg gaaaaagatt tattgcacta cgtgagctct   420
gtagcatttg caaggcaaac cgcccccaat ggcaagacc acagtactgc aaagcaatgt   480
caagagtttg aagagtgcat aggtgggcct gaaaaaatgg ctcaattaac agggtccaga   540
gcccatttta gatttactgg tcctcaaatt ctgaaaattg cacaattaga accagaagct   600
tacgaaaaaa caaagaccat ttctttagtg tctaattttt tgacttctat cttagtgggc   660
```

```
catcttgttg aattagagga ggcagatgcc tgtggtatga acctttatga tatacgtgaa      720
agaaaattca gtgatgagct actacatcta attgatagtt cttctaagga taaaactatc      780
agacaaaaat taatgagagc acccatgaaa aatttgatag cgggtaccat ctgtaaatat      840
tttattgaga agtacggttt caatacaaac tgcaaggtct ctcccatgac tggggataat      900
ttagccacta tatgttcttt accectgegg aagaatgacg ttctegtttc cctaggaaca      960 agtactacag ttcttctggt caccgataag tatcacccct ctccgaacta tcatcttttc     1020
attcatccaa ctctgccaaa ccattatatg ggtatgattt gttattgtaa tggttctttg     1080
gcaagggaga ggataagaga cgagttaaac aaagaacggg aaaataatta tgagaagact     1140
aacgattgga ctcttttaa tcaagctgtg ctagatgact cagaaagtag tgaaaatgaa      1200
ttaggtgtat attttcctct gggggagatc gttcctagcg taaaagccat aaacaaaagg     1260
gttatcttca atccaaaaac gggtatgatt gaaagagagg tggccaagtt caaagacaag     1320
aggcacgatg ccaaaaatat tgtagaatca caggctttaa gttgcagggt aagaatatct     1380
cccctgcttt cggattcaaa cgcaagctca caacagagac tgaacgaaga tacaatcgtg     1440
aagtttgatt acgatgaatc tccgctgcgg gactacctaa ataaaaggcc agaaaggact     1500
ttttttgtag gtggggcttc taaaaacgat gctattgtga agaagtttgc tcaagtcatt     1560
ggtgctacaa agggtaattt taggctagaa acaccaaact catgtgccct tggtggttgt     1620
tataaggcca tgtggtcatt gttatatgac tctaataaaa ttgcagttcc ttttgataaa     1680
tttctgaatg acaattttcc atggcatgta atggaaagca tatccgatgt ggataatgaa     1740
aattgggatc gctataattc caagattgtc cccttaagcg aactggaaaa gactctcatc     1800
taa                                                                   1803
```

METHOD FOR PRODUCING MYCOSPORINE-LIKE AMINO ACID USING MICROBES

TECHNICAL FIELD

The present invention relates to a method for producing a mycosporine-like amino acid using a microorganism, a mycosporine-like amino acid produced by the method, and an UV-absorbing agent comprising the mycosporine-like amino acid.

BACKGROUND ART

It is known that ultraviolet rays (UV) induce acute skin reactions such as erythema, skin aging, and skin cancer. The ultraviolet rays contained in sunlight are classified, based on the wavelength, into three types: UV-A (320 nm-400 nm), UV-B (280 nm-320 nm) and UV-C (200-280 nm). Among them, UV rays having an effect on living bodies are UV-A and UV-B; whereas UV-C is harmless since it normally cannot pass through the atmosphere.

It is known that UV-B is a main cause of sunburn in the outdoors and has relatively larger energy than UV-A. When UV-B is absorbed by skin layer, it reaches the stratum corneum and the epidermis, and causes acute skin pigmentation such as spots and freckles. UV-B is also known to cause immunosuppression involved in aging and onset of skin cancer.

UV-A has a longer wavelength than UV-B and the energy is lower; however, UV-A penetrates into a further deeper portion of the skin than UV-B and is known to reach the dermis. As a result, not only acute skin pigmentation such as spots and freckles but also reduction in elasticity of the dermis (actinic elastosis) is caused, with the result that early skin aging such as wrinkles and sagging is induced. Furthermore, in recent years, it has been found that UV-A also causes immunosuppression and is involved in precancerous skin lesion and onset of skin cancer.

UV-B varies in amount depending upon e.g., season, weather and latitude; whereas the amount of UV-A reached the surface of the earth is constant throughout the year. Therefore, it is important to protect the skin also from UV-A.

UV protectors currently available in the market are divided into UV-absorbing agents and UV scattering agents. The UV-absorbing agents convert the UV energy into heat energy and release it, and include, for example, an organic compound such as 4-tert-butyl-4'-methoxydibenzoylmethane. The UV scattering agents contain an inorganic particle such as titanium oxide ($TiO_2$) and zinc oxide (ZnO), and when the UV scattering agent is applied to the skin, the inorganic particles present on the skin reflect UV rays and serve as a UV barrier.

The UV-absorbing agents have problems: (1) the UV-absorbing agents are easily decomposed by light and have poor stability, (2) molecular excitation occurs and accelerates production of melanin to cause itchiness and allergy, and (3) a bad image is given to the users due to chemically synthesized substances. The UV scattering agents have the problems: (1) skin likely looks white when applied and the user tends to feel heavy in the skin, (2) generation of active oxygen is induced, and (3) pores of skin are closed and skin respiration may be inhibited. Because of these problems, development of a naturally derived safe UV-absorbing substance has been highly expected.

Mycosporine-like amino acids (hereinafter, referred to as MAAs) are natural UV-A absorbing substances, which are known to be present in a wide variety of aquatic organisms such as coral, red algae, fish viscera and microalgae. Among others, shinorine is known to be the most effective natural UV-A absorbing substance. Chemical synthesis of an MAA has been tried; however it requires long and complicated processes (Patent Document 1). Also, production of an MAA by light irradiation of cyanobacteria has been tried; however, the production amount of MAA is extremely low (Non-Patent Document 1). Further, extraction of MAAs from natural products such as laver, algae and shellfish has been tried; however, a sufficient yield has not been obtained in these cases (Patent Document 2 and Non-Patent Documents 2 to 4). Furthermore, extraction and production from natural products are easily influenced by climate conditions and mostly unstable, and thus, it is difficult to obtain MAAs stably in a large amount. In the meantime, microbial biosyntheses of MAAs have been tried; however, these processes require disruption of cells and extraction with an organic solvent in order to obtain biosynthesized MAAs from the microbial cells (Patent Document 3 and Non-Patent Documents 5 and 6). Thus, the operation becomes complicated and an operation for removing debris derived from microbial cells is further required.

CITATION LIST

Patent Documents

Patent Document 1: WO02/39974
Patent Document 2: JP2013-518871A
Patent Document 3: JPH6-62878A

Non-Patent Documents

Non-Patent Document 1: World J. Microbiol. Biotechnol. (2008) 24: 3111-3115
Non-Patent Document 2: Marine Biology 108, 157-166 (1991)
Non-Patent Document 3: Photomedicine and Photobiology (2002), 24, 39-42
Non-Patent Document 4: Tetrahedron: Letters (1979), 3181-3182
Non-Patent Document 5: FEMS Yeast Res. (2011), 11: 52-59
Non-Patent Document 6: J. Bacteriol. (2011), 193 (21): 5923-5928

SUMMARY OF INVENTION

Problem to be Solved by the Invention

The problems to be solved by the present invention include providing a method of producing a naturally derived safe UV-absorbing substance stably and in a large amount.

Means to Solve the Problem

The inventors have established a method of biosynthesizing an MAA by using a microorganism extracellularly producing the MAA, and obtaining the MAAs in a large amount from the extracellular culture solution. The inventors found that a naturally derived MAA can be more relatively easily and stably produced by this method than conventional methods, and have completed the present invention.

That is, the present invention provides:

(1) A method for producing a mycosporine-like amino acid, comprising the steps of:
culturing a microorganism extracellularly producing the mycosporine-like amino acid,
separating the microbial cell and extracellular culture solution, and
recovering the mycosporine-like amino acid from the extracellular culture solution;

(2) The method according to (1), further comprising a step of purifying the recovered mycosporine-like amino acid;

(3) The method according to (1) or (2), wherein the microorganism is a microorganism belonging to *Escherichia coli*, yeast, actinomycetes, microalgae or labyrinthulea;

(4) The method according to (3), wherein the microorganism is an actinomycete;

(5) The method according to (4), wherein the actinomycete belongs to the genus *Streptomyces*, the genus *Actinosynnema*, the genus *Pseudonocardia* or the genus *Corynebacterium*;

(6) The method according to (3), wherein the microorganism is labyrinthulea and belongs to the genus *Aurantiochytrium*;

(7) The method according to (3), wherein the microorganism is yeast and belongs to the genus *Saccharomyces*;

(8) The method according to any one of (1) to (7), wherein the microorganism comprises heterologous mycosporine-like amino acid biosynthetic enzyme genes;

(9) The method according to (8), wherein the mycosporine-like amino acid biosynthetic enzyme genes are composed of amir_4256, amir_4257, amir_4258 and amir_4259 genes derived from *Actinosynnema mirum*;

(10) The method according to (8), wherein a codon of at least one gene of the mycosporine-like amino acid biosynthetic enzyme genes is modified for a microorganism into which the gene is to be introduced;

(11) The method according to (9) or (10), wherein the microorganism is *Streptomyces avermitilis* MA-4680 (NITE accession number: NBRC 14893), *Streptomyces lividans* 1326 (NITE accession number: NBRC 15675), *Corynebacterium glutamicum* ATCC13032 (NITE accession number: NBRC 12168), *Aurantiochytrium* sp. SAM2179 (FERM BP-5601), *Escherichia coli* JM109 or *Saccharomyces cerevisiae* YPH499XW;

(12) A mycosporine-like amino acid represented by Formula 1:

[Compound 1]

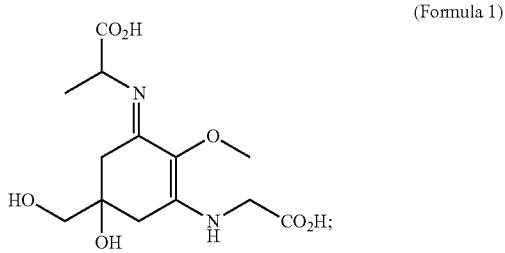

(Formula 1)

(13) The mycosporine-like amino acid according to (12), produced by the method according to any one of (1) to (11);

(14) A UV-absorbing composition comprising a mycosporine-like amino acid produced by the method according to any one of (1) to (11) or the mycosporine-like amino acid according to (12) or (13) and a component acceptable for cosmetics, quasi-drugs or pharmaceuticals; and

(15) A composition for preventing at least one symptom or disease selected from the group consisting of acute skin reactions, skin aging and skin cancer, comprising a mycosporine-like amino acid produced by the method according to any one of (1) to (11) or the mycosporine-like amino acid according to (12) or (13) and a component acceptable for cosmetics, quasi-drugs or pharmaceuticals.

Effects of the Invention

According to the present invention, it is possible to produce an MAA more easily than a complicated conventional chemical synthesis having many steps. It is also possible to obtain an MAA in a larger amount than conventional methods of obtaining MAAs from a natural product such as laver and shellfish. Thus, an MAA can be stably produced. In addition, since an MAA can be obtained from extracellular culture solution, a purification step is simplified compared to methods of obtaining MAAs by disruption of a microbial cell. As a result, a highly purified MAA can be quickly obtained in a high yield.

DESCRIPTION OF EMBODIMENTS

Figure 1A:
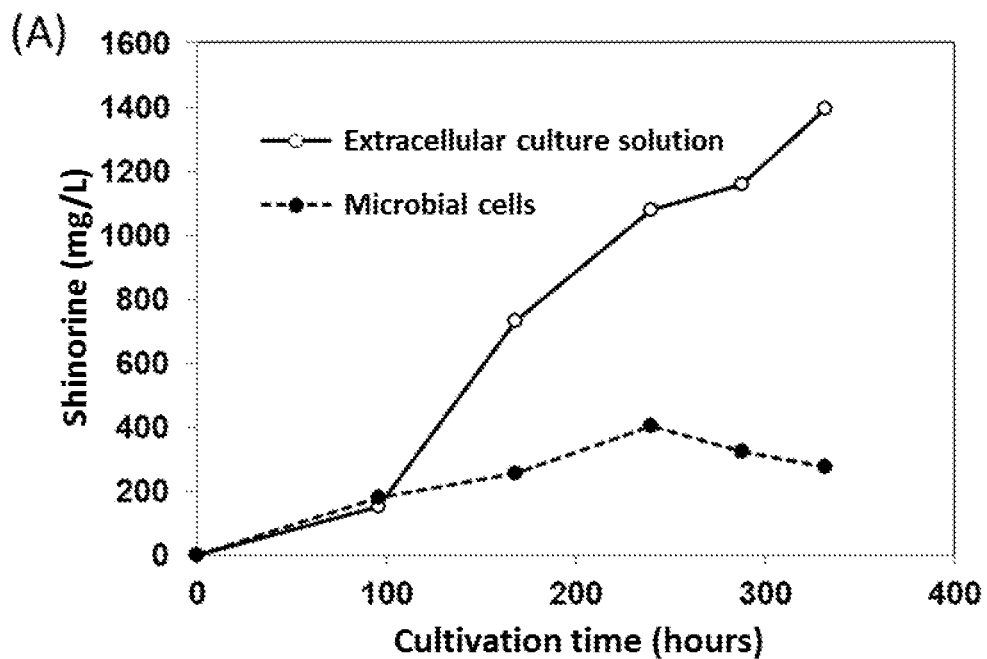
FIGS. 1A and 1B show the amounts of shinorine and porphyra-334 produced by *Streptomyces avermitilis* MA-4680 (NITE accession number: NBRC 14893) in comparison with respect to the production in extracellular culture solution and in microbial cells. (A) Shinorine; (B) Porphyra-334. Solid line•white circle: Extracellular culture solution; Broken line•black circle: Microbial cells.

In one aspect, the present invention provides a method for producing an MAA comprising the steps of: culturing a microorganism extracellularly producing the MAA; separating the microbial cell and extracellular culture solution; and recovering the MAA from the extracellular culture solution.

According to the method of the present invention, an MAA is obtained from a culture supernatant of a microorganism. Thus, the MAA can be obtained in a larger amount than conventional methods using a natural product. In addition, the method of the present invention does not require a step of disrupting a microbial cell. Thus, the time and cost can be reduced compared to conventional methods of extracting MAAs by disrupting natural products such as algae. In a method comprising a disrupting step, contaminants resulting from the disruption are carried in subsequent processes and complicate the following purification processes. However, in the method of the present invention, such carry-in of contaminants can be prevented, with the result that the subsequent purification processes can be simplified. As a result, the time and cost required for purification can be both reduced.

In the present invention, the term "mycosporine-like amino acid (hereinafter referred to as MAA)" is a general term of a compound having a cyclohexenone or cyclohexeneimine skeleton (optionally having a substituent) to which amino acid(s) is/are bound.

Examples of the MAA include, but are not limited to, shinorine (the following Formula 2), porphyra-334 (the following Formula 3), asterina-330 (the following Formula 4), palythene (the following Formula 5), palythine (the following Formula 6), mycosporine-glycine (the following Formula 7), mycosporine-glycine:valine (the following Formula 8) and mycosporine serinol (the following Formula 9).

[Compound 2]

(Formula 2)

[Compound 3]

(Formula 3)

[Compound 4]

(Formula 4)

[Compound 5]

(Formula 5)

[Compound 6]

(Formula 6)

[Compound 7]

(Formula 7)

[Compound 8]

(Formula 8)

[Compound 9]

(Formula 9)

As used herein, examples of the "microorganism (microbe)" include, but are not limited to, bacteria such as actinomycetes, *Escherichia coli* and *Bacillus subtilis*; fungi such as molds and yeast; microalgae such as cyanobacteria; and labyrinthulea.

The term "actinomycete" refers to a gram-positive bacterium belonging to the Actinobacteria. Examples of the "actinomycete" include, for example, the genus *Streptomyces* such as *Streptomyces lividans, Streptomyces violaceoruber, Streptomyces coelicolor, Streptomyces avermitilis* and *Streptomyces griseus*; the genus *Actinosynnema* such as *Actinosynnema pretiosum* and *Actinosynnema mirum*; the genus *Pseudonocardia* such as *Pseudonocardia autotrophica, Pseudonocardia thermophila*; and the genus *Corynebacterium* such as *Corynebacterium glutamicum*. The actinomycetes can be separated from e.g., soil, or obtained from microorganism depositary institutions.

The "yeast" includes ascosporogenous yeast, basidiosporogenous yeast, and yeast belonging to the imperfect fungi. Examples of the yeast include, for example, the genus *Saccharomyces* such as *Saccharomyces cerevisiae*; the genus *Schizosaccharomyces* such as *Schizosaccharomyces pombe*; the genus *Phaffia* such as *Phaffia rhodozyma*; the genus *Kluyveromyces* such as *Kluyvercmyces marxianus*; the genus *Yarrowia* such as *Yarrowia lipolytica*; the genus *Pichia* such as *Pichia stipitis*; and the genus *Candida* such as *Candida utilis*. The yeast can be separated from e.g., plants, animals and soil, or obtained from microorganism depositary institutions.

The term "microalgae" refers to algae having microscopic structure except sea algae which is multicellular organism. The term "algae" refer to all the oxygenic photosynthetic organisms except moss plants, ferns and seed plants principally living on the ground. The algae include various unicellular organisms and multicellular organisms. For example, the algae include sea algae; Cyanobacteria belonging to prokaryotes; and Glaucophyta, Rhodophyta (red algae) and Chlorophyta belonging to eukaryotes. The microalgae also include a group body formed of a plurality of cells. The microalgae are not always living in water and those living in soil or on body surfaces of animals are included. Examples of the "Cyanobacteria" include, for example, *Anabaena variabilis, Nostoc punctiforme, Nostoc linckia, Nostoc commune, Nostoc verrucosum* and *Nostoc muscorum*. The Cyanobacteria can be separated from nature, or obtained from microorganism depositary institutions.

The "labyrinthulea" is an amoeboid eukaryote included in stramenopiles. Examples of the labyrinthulea include, for example, the genus *Aurantiochytrium*, the genus *Schizochytrium*, the genus *Thraustochytrium* and the genus *Ulkenia*. The labyrinthulea can be separated from nature such as seaweeds and land plants, or obtained from microorganism depositary institutions.

As used herein, the term "microorganism extracellularly producing a mycosporine-like amino acid (microbes that produce MAA on the outside of bacterial cells)" refers to a microorganism having ability to biosynthesize and extracellularly produce an MAA, for example, a microorganism having an MAA biosynthetic enzyme gene. Such a "microorganism extracellularly producing a MAA" may be a wild-type or an artificially mutated strain. Examples of an artificially mutation treatment include genetic recombination, UV irradiation, X-ray irradiation and treatment with a mutagenesis agent. Furthermore, the microorganism extracellularly producing a MAA may be a spontaneous mutant. The "microorganism extracellularly producing the MAA" includes a microorganism having a homologous or heterologous MAA biosynthetic enzyme gene. For example, a microorganism into which a heterologous MAA biosynthetic enzyme gene is introduced by genetic recombination may be used. For introducing a heterologous gene into a microorganism, a method widely known in the art may be used.

In the case where a homologous or heterologous MAA biosynthetic enzyme gene is introduced into a microorganism by genetic recombination, for example, a promoter, a 5' untranslated region (UTR), a marker gene for transformant selection, a 3' untranslated region (UTR), or a part thereof may be introduced together with the gene. In this case, a promoter etc. widely known to those skilled in the art as those used in the microorganism may be used. Furthermore, a codon of the gene may be appropriately modified depending upon the codon usage in the microorganism into which the MAA biosynthetic enzyme gene is to be introduced. Codon usage in a microorganism can be checked by those skilled in the art, for example, by using Codon Usage Database (Hypertext Transfer Protocol (HTTP)://WorldWideWeb.kazusa.or.jp/codon/) of Kazusa DNA Research Institute. Alternatively, codon usage can be checked by using the gene sequence design program, GeneOptimizer® provided by GENEART AG, etc. Further, based on the information of codon usage thus obtained, the codon of a subject gene can be optimized by a usual practice.

Examples of the mycosporine-like amino acid biosynthetic enzyme gene include, but are not, limited to, amir_4256 (SEQ ID NO: ami_4257 (SEQ ID NO: 2), amir_4258 (SEQ ID NO: 3) and amir_4259 (SEQ ID NO: 4) genes derived from *Actinosynnema mirum* DSM43827; pseP1_010100031425 (SEQ ID NO: 5), pseP1_010100031430 (SEQ ID NO: 6), pseP1_010100031435 (SEQ ID NO: 7) and pseP1_010100031440 (SEQ ID NO: 8) genes derived from *Pseudonocardia* sp. P1; Ava3855, Ava3856, Ava3857 and Ava3858 genes derived from *Anabaena variabilis* ATCO29413 (see, Balskus E P et al., Science, (2010), 329: 1633-1656); and mysA, mysB, mysC and mysD genes derived from *Nostoc punctiforme* ATCC29133 (see, JOURNAL OF BACTERIOLOGY, November 2011, Vol. 193, No. 21, p. 5923-5928). For example, in an embodiment where a labyrinthulea is used, codon-optimized amir_4256 (SEQ ID NO: 9), codon-optimized amir_4257 (SEQ ID NO: 10), codon-optimized amir_4258 (SEQ ID NO: 11) and codon-optimized amir_4259 (SEQ ID NO: 12) genes are used as the mycosporine-like amino acid biosynthetic enzyme genes.

In an embodiment of the present invention, the microorganism used herein is a microorganism belonging to *Escherichia coli*, yeast, actinomycetes, microalgae or labyrinthulea. For example, the microorganism used herein is a microorganism belonging to *Escherichia coil*, yeast, actinomycete, or labyrinthulea.

In an embodiment where an actinomycete is used, a microorganism belonging to the genus *Streptomyces*, the genus *Actinosynnema*, the genus *Pseudonocardia* or the genus *Corynebacterium* is used. In other embodiment, a microorganism belonging to the genus *Streptomyces* or the genus *Corynebacterium* is used. In another embodiment, *Streptomyces lividans, Streptomyces avermitilis* or *Corynebacterium glutamicum* is used. In yet another embodiment, an actinomycete comprising amir_4256, amir_4257, amir_4258 and amir_4259 genes derived from *Actinosynnema mirum* is used. For example, *Streptomyces avermitilis* MA-4680 (NITE accession number: NBRC 14893, deposited with the Patent Microorganisms Depositary (NPMD), National Institute of Technology and Evaluation (NITE), located at 2-5-8, Kazusakamatari, Kisarazu-shi, Chiba, Japan); *Streptomyces lividans* 1326 (NITE accession number: NBRC 15675, deposited with the Patent Microorganisms Depositary (NPMD), National Institute of Technology and Evaluation (NITE), located at 2-5-8, Kazusakamatari, Kisarazu-shi, Chiba, Japan); or *Corynebacterium giutamicum* ATCC13032 (NITE accession number: NBRC 12168, deposited with the Patent Microorganisms Depositary (NPMD), National Institute of Technology and Evaluation (MITE), located at 2-5-8, Kazusakamatari, Kisarazu-shi, Chiba, Japan), which comprises amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum*, is used.

In an embodiment where labyrinthulea is used, a microorganism belonging to the genus *Aurantiochytrium*, the genus *Schizochytrium*, the genus *Thraustochytrium* or the genus *Ulkenia* is used. In other embodiment, a microorganism belonging to the genus *Aurantiochytrium* is used. In another embodiment, labyrinthulea comprising amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* is used. In yet another embodiment, labyrinthulea comprising codon-modified (for labyrinthulea) amir_4256, amir_4257, amir_4258 and amir_4259 genes is used. In other embodiment, *Aurantiochytrium* sp. SAM2179 (FERM BP-5601) comprising codon-modified (for labyrinthulea) amir_4256, amir_4257, amir_4258 and amir_4259 genes is used (note that, this strain was deposited as *Ulkenia* sp. SAM2179, and the classification of this strain was changed at a later date after completion of genome sequencing).

In an embodiment where yeast is used, a microorganism belonging to the genus *Saccharomyces*, the genus *Schizosaccharomyces*, the genus *Phaffia*, the genus *Kluyveromyces*, the genus *Yarrowia*, the genus *Pichia* or the genus *Candida* is used. In other embodiment, a microorganism belonging to the genus *Saccharomyces* is used. In another embodiment, yeast having a xylose-assimilating gene is used. In yet another embodiment, yeast compressing amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* DSM43827 is used. In other embodiment, *Saccharomyces cerevisiae* YPH499XW having a xylose-assimilating gene and comprising amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* DSM43827 is used.

In an embodiment where *Escherichia coli* is used, *Escherichia coli* comprising amir_4256 (SEQ ID NO: 1), amir_4257 (SEQ ID NO: amir_4258 (SEQ ID NO: 3) and amir_4259 (SEQ ID NO: 4) genes derived from *Actinosynnema mirum* DSM43827 is used. In another embodiment, *Escherichia coli* JM109 comprising amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* DSM43827 is used.

As used herein, the term, "microbial cell" refers to a cell of a microorganism. In addition, as used herein, the term "extracellular culture solution (fluid)" refers to a part obtained by moving the microbial cell from the culture solution obtained by culturing a microorganism. That is, the extracellular culture solution comprises various components contained in the culture medium used in culture and substances produced by a microorganism during the culture.

A method for separating a microbial cell and extracellular culture solution is appropriately selected by those skilled in the art. For example, a microbial cell and extracellular culture solution may be separated by subjecting the culture solution obtained by culturing a microorganism to centrifugation. Centrifugation conditions such as temperature, time and speed vary depending upon the type of microorganism and the conditions well-known to those skilled in the art may be used. Alternatively, a microbial cell and extracellular culture solution may be separated by filtering the culture solution obtained by culturing a microorganism by use of an appropriate filtration membrane. Alternatively, microbial cells may be aggregated with the help of an appropriate aggregating agent and thereafter subjected to centrifugation filtration.

Recovering an MAA extracellular culture solution refers to obtaining a liquid mainly containing an MAA by removing various components contained in the culture medium used in culture that are contained in the extracellular culture solution and substances except the MAA produced by a microorganism during culture. A method for recovering an MAA from extracellular culture solution is also appropriately selected by those skilled in the art. For example, an MAA can be recovered from extracellular culture solution by filtration with a membrane or by using an appropriate medium. The medium is appropriately selected by those skilled in the art. In a preferable embodiment, an aqueous solvent is used. Examples of the aqueous solvent include, but are not limited to, acidic, neutral or alkaline aqueous solution or an aqueous solution containing a salt.

In other aspect, the present invention provides the method as mentioned above further comprising a step of purifying the recovered MAA. For purification of MAA, a method for purifying a metabolite from a culture of microorganism that is well-known to those skilled in the art may be used. For example, a purified MAA may be obtained by extraction with an organic solvent, a treatment with activated carbon, gel filtration, ion exchange column chromatography, high performance liquid chromatography (HPLC), crystallization and/or electrodialysis.

In the present invention, a culture medium may be neutralized, if necessary. As a neutralizer, those known in the art may be used, including for example, a carbonate such as calcium carbonate, magnesium carbonate, sodium carbonate and sodium hydrogen carbonate; a hydroxide such as sodium hydroxide, potassium hydroxide, calcium hydroxide and magnesium hydroxide; ammonia; quicklime, limestone and hydrated lime. In one embodiment, the neutralizer used in the present invention is a carbonate such as calcium carbonate, magnesium carbonate and sodium hydrogen carbonate. The neutralizer may be added to a culture medium before or during culture. The neutralizer may be added continuously or intermittently. The addition amount of neutralizer can be readily determined by measuring pH of the culture medium. The pH of the culture medium can be measured by a conventionally known method, for example, by a pH meter.

In the present invention, culture medium and other culture conditions (e.g., temperature, time, pH, stirring or not) for culturing a microorganism can be appropriately selected by those skilled in the art depending upon the type of the microorganism to be cultured.

In the case where an actinomycete is used, for example, a semi-synthetic medium for an actinomycete (6% glucose, 0.2% NaCl, 0.05% $K_2HPO_4$, 0.01% $MgSO_4.7H_2O$, 0.2% $(NH_4)_2SO_4$, 0.2% yeast extract, 0.005% $FeSO_4.7H_2O$, 0.005% $MnSO_4.4H_2O$, 0.005% $ZnSO_4.7H_2O$, 0.5% $CaCO_3$), TSB culture medium (0.25% glucose, 1.7% pancreatic digest of casein, 0.3% papaic digest of soybean, 0.5% NaCl, 0.25% $K_2HPO_4$), or SYN culture medium (0.7% casamino acid, 0.2% yeast extract, 0.264% $(NH_4)_2SO_4$, 0.238% $KH_2PO_4$, 0.556% $K_2HPO_4$, 0.1% $MgSO_4.7H_2O$, 0.0064% $CuSO_4.5H_2O$, 0.0011% $FeSO_4.7H_2O$, 0.0079% $MnSO_4.4H_2O$, 0.0015% $ZnSO_4.7H_2O$, 0.5% $CaCO_3$) may be used. In the case where *Escherichia coli* is used, for example, LB culture medium, 2×YT culture medium, NZY culture medium, M9 culture medium, SOC culture medium, or YPD culture medium may be used. In the case where yeast is used, for example, SD culture medium, YPD culture medium or YPAD culture medium may be used.

The above culture medium may be appropriately modified in order to improve the culture state of a microorganism. For example, a culture medium may be modified by increasing the initial concentration of glucose in the culture medium or by adding Trace element solution (×200) ($CuSO_4.5H_2O$ 64 mg, $FeSO_4.7H_2O$ 11 mg, $MnSO_4.4H_2O$ 79 mg, $ZnSO_4.7H_2O$ 15 mg/50 mL).

In another aspect, the present invention provides an MAA produced by the aforementioned method of the present invention. The MAA produced by the present invention is not limited to MAAs whose structures are already determined but an MAA whose structure is newly determined may be included. In one embodiment, the former MAA may be shinorine, porphyra-334, palythine, mycosporine serinol or mycosporine glycine, or any combination thereof. Examples of the MAA having new structure include mycosporine-glycine-alanine (the following Formula 10). Accordingly, in one embodiment, the present invention provides mycosporine-glycine-alanine. In other embodiment, the present invention provides mycosporine-glycine-alanine produced by the aforementioned method of the present invention.

[Compound 10]

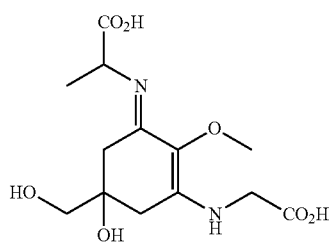

(Formula 10)

As a method for identifying an MAA, a conventionally known method may be used. For example, high-performance liquid chromatography-time-of-flight mass spectrometry (HPLC-TOFMS) may be used. Similarly, as a method for identifying a novel MAA, a conventionally known method may be used. For example, a novel MAA may be identified by using High Resolution Mass Spectrometry (HR-MS) and Nuclear Magnetic Resonance (NMR) in combination. Alternatively, an MAA may be identified by using HPLC based on the retention time and the results of a UV spectrum. Alternatively, a novel MAA may be identified by measuring a UV absorption spectrum and accurate mass by using HPLC apparatus equipped with a photodiode array detector and an HR-MS detector.

The present invention further provides a UV-absorbing composition comprising an effective amount of MAA produced by the method of the present invention or mycosporine-glycine-alanine as mentioned above as an active ingredient and another component acceptable for cosmetics, quasi-drugs or pharmaceuticals. The UV-absorbing composition of the present invention can be used not only in the fields of cosmetics and pharmaceuticals but also as a paint composition and another coating agent. For example, in the case where the UV-absorbing composition of the present invention is applied to human skin, the composition may comprise the MAA produced by the method of the present invention in an amount of about 0.05 to 10 wt %, an oil phase medium (about 5 to 40 wt %), an emulsifier (about 1 to 10 wt %), a small amount of an auxiliary agent and an aqueous phase medium such as water.

The present invention further provides a composition, for preventing at least one symptom or disease selected from the group consisting of acute skin reactions, skin aging and skin cancer, comprising an MAA produced by the method of the present invention or mycosporine-glycine-alanine as mentioned above and a component acceptable for cosmetics, quasi-drugs or pharmaceuticals. The composition comprises an effective amount of MAA produced by the method of the present invention as an active ingredient.

The composition of the present invention as mentioned above may be prepared in the form that ordinary cosmetics or pharmaceuticals for skin application may take, such as cream, lotion, paste, ointment, emulsion (oil-in-water emulsion, water-in-oil emulsion, multiple emulsion, microemulsion, PET-emulsion, Pickering emulsion), gel (hydrogel, alcohol gel), suspension, foam, spray, tablet or powder.

Examples of the component that can be comprised in the composition of the present invention as mentioned above and acceptable for cosmetics, quasi-drugs or pharmaceuticals include auxiliaries and additives of ordinary cosmetics, quasi-drugs or pharmaceuticals, for example, a preservative such as benzalkonium chloride, benzethonium chloride, hexamethonium chloride, butyl alcohol, benzyl alcohol, alkyl parabens such as methyl paraben or propyl paraben, catechol, resorcinol, cyclohexanol and m-cresol; an antioxidant such as ascorbic acid and methionine; a buffer such as phosphoric acid, citric acid and other organic acids; an emulsifier such as a sorbitan ester, Tween®, silicon polyol, potassium stearate and an ethoxylated fatty acid ester; an emulsion stabilizer; anionic, cationic, nonionic or amphoteric polymer; a chelating agent such as EDTA; oil phase medium (a hydrocarbon-based oil such as a mineral oil, a paraffin wax, a natural oil, a silicone oil, a fatty acid ester such as isopropyl palmitate, a fatty alcohol such as stearyl alcohol); a thickener; a humectant; an emollient; a surfactant such as polyethylene glycol (PEG); an acidifying or basifying agent; a flavor; a fragrance; a dye; a coloring agent; or other components generally blended in cosmetics, quasi-drugs or pharmaceuticals.

EXAMPLES

The present invention will be described in detail and specifically by way of examples; however, they are provided for illustrative purposes only and should not be construed as limiting the present invention.

Example 1

1. Production of MAA using *Streptomyces*

The present inventors produced MAAs using *Streptomyces lividans* and *Streptomyces avermitilis*. In addition, the present inventors compared the production amount of MAA with respect to the production in extracellular culture solution and in microbial cells (FIG. 1).

1-1. Introduction of MAA Biosynthetic Enzyme Genes 1-1-1. Introduction of MAA Biosynthetic Enzyme Genes into *Streptomyces lividans*

As MAA biosynthetic enzyme genes, amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* DSM43827 were used. These genes were ligated to a vector having pIJ101 ori under the control of PLD promoter (see, JP2002-51780A) to prepare a gene expression vector. *Streptomyces lividans* 1326 (NITE accession number: NBRC 15675) was transformed with the gene expression vector to obtain an MAA producing strain. *Streptomyces lividans* was transformed in accordance with a conventionally known method.

1-1-2. Introduction of MAA Biosynthetic Enzyme Genes into *Streptomyces avermitilis*

The aforementioned genes: amir_4256 (SEQ ID NO: 1), amir_4257 (SEQ ID NO: 2), amir_4258 (SEQ ID NO: 3) and amir_4259 (SEQ ID NO: 4), were introduced into Streptomyces avermitilis MA-4680 (NITE accession number: NBRC 14893) by homologous recombination obtain an MAA producing strain. The homologous recombination of Streptomyces avermitilis was carried out in accordance with a conventionally known method.

1-2. Pre-Culture of *Streptomyces lividans* and *Streptomyces avermitilis*

To 5 mL of AVM culture medium (see the following Table 1), a glycerol stock of a spore of *Streptomyces lividans* 1326 or *Streptomyces avermitilis* MA-4680 having the MAA biosynthetic enzyme genes, which was prepared in Section 1-1 above, was added. These actinomycetes were cultured at 28° C. and shaken at 160 rpm for 48 hours.

TABLE 1

| AVM culture medium (pH 7.5) | |
|---|---|
| Glucose | 5 g (0.5%) |
| Soy-bean flour | 15 g (1.5%) |
| Yeast extract | 5 g (0.5%) |
| Total | 1000 mL |

1-3. Main Culture of *Streptomyces lividans* and *Streptomyces avermitilis*

The pre-culture solution (an amount corresponding to 0.1%) was added to 50 mL of TSBt culture medium (see the following Tables 2 to 4) contained in a 500 mL baffled flask. Glucose was further added to the TSBt culture medium at the starting of the culture such that the initial concentration of glucose became 50 g/L. These strains were cultured at 28° C. and shaken at 160 rpm for two weeks.

TABLE 2

| TSB culture medium | |
|---|---|
| Pancreatic digest of casein | 17 g (1.7%) |
| Papaic digest of soybean | 3 g (0.3%) |
| Glucose | 25 g (0.25%) |
| NaCl | 5 g (0.5%) |
| $K_2HPO_4$ | 2.5 g (0.25%) |
| Total | 1000 mL |

TABLE 3

| TSBt culture medium | |
|---|---|
| TSB culture medium | 50 mL |
| Trace element solution (×200) | 0.25 mL (amount corresponding to 0.5%) |

TABLE 4

| Trace element solution (×200) | |
|---|---|
| $CuSO_4 \cdot 5H_2O$ | 64 mg |
| $FeSO_4 \cdot 5H_2O$ | 11 mg |
| $MnSO_4 \cdot 4H_2O$ | 79 mg |
| $ZnSO_4 \cdot 7H_2O$ | 15 mg |
| Total | 50 mL |

1-4. Measurement of MAA

During the main culture, 1 mL of the culture solution was sampled at a predetermined time and the turbidity of the sampled culture solution was measured at 600 nm. The sampled culture solution was centrifuged at 14000 rpm for 20 minutes to separate extracellular culture solution and a precipitate (microbial cells). The separated extracellular culture solution was used as an extracellular culture solution-sample. Methanol (1 mL) was added to the separated microbial cells, and the microbial cells were disrupted by stirring and then subjected to centrifugation to recover the supernatant (microbial cell-sample). The production amounts of shinorine and porphyra-334 in each of the extracellular culture solution-samples and the diluted microbial cell-samples were measured by HPLC. The measurement conditions of HPLC are as shown in the following Table.

TABLE 5

| Column: | HYPERCARB (R) (3 μm; 2.1 ϕ mm × 100 mm) (manufactured by Thermo Scientific) |
|---|---|
| Solvent: | Solvent A: 0.1M triethylamine acetate salt (TEAA) |
| | Solvent B: 100% acetonitrile |
| Gradient conditions: | 0-4 minutes 6% Solvent B |
| | 4-10 minutes 6-15% Solvent B linear gradient |
| | 10-15 minutes 15-80% Solvent B linear gradient |
| | 15-20 minutes 80-6% Solvent B linear gradient |
| | 20-35 minutes 6% Solvent B |
| Detection wavelength: | 334 nm |
| Standard sample: | Shinorine: manufactured by Mibelle AG Biotechnology Product name: Helioguard 365 |
| | Porphyra-334: manufactured by Mibelle AG Biotechnology Product name: Helioguard 365 |
| Flow rate: | 0.2 mL/minute |
| Retention time: | Shinorine: around 6 minutes |
| | Porphyra-334: around 5 minutes |

1-5. Results

Figure 1B:
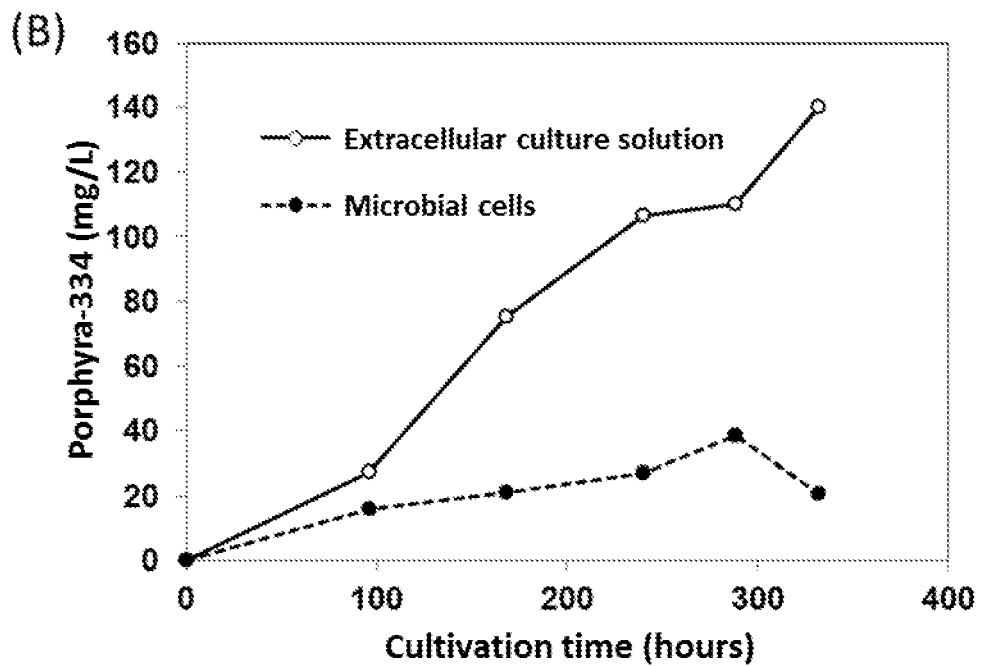

The results of *Streptomyces avermitilis* MA-4680 are shown in FIG. 1. FIG. 1(A) shows the distribution of shinorine; whereas FIG. 1(B) shows the distribution of porphyra-334. It was verified that both shinorine and porphyra-334 are more largely distributed in the extracellular culture solution than in the microbial cells. From these results, it was demonstrated that the production amount of shinorine in the extracellular culture solution is about 5 times as large as the production amount in microbial cells at the time of two weeks from initiation of the culture. Similarly, it was demonstrated that the production amount of porphyra-334 in the extracellular culture solution is about 7 times as large as the production amount in the microbial cells. In *Streptomyces lividans* 1326, extracellular production amount of shinorine was 150 mg/L and intracellular production amount was 50 mg/L at the time of about one week from initiation of the culture. The extracellular production amount thereof was 510 mg/L and the intracellular production amount thereof was 105 mg/L at the time of about two weeks from initiation of the culture.

Example 2

2. Production of Novel MAA (Mycosporine-Glycine-Alanine)

2-1. *Streptomyces avermitilis* producing an MAA was cultured in the same manner as in Example 1 for two weeks. The initial glucose concentration was set at 100 g/L. As a result, in the extracellular culture solution, mycosporine-glycine-alanine was produced as a novel MAA in addition to shinorine and porphyra-334. The production amount of mycosporine-glycine-alanine obtained was 25 mg/L. HPLC analysis was carried out in the conditions shown in Table 5, and as a result, the retention time was around 15 minutes.

2-2. Identification of Novel MAA (Mycosporine-Glycine-Alanine)

The novel MAA was identified as follows. Using an HPLC apparatus equipped with a photodiode array detector and an HR-MS detector, UV absorption spectrum and the accurate mass were measured. The measurement conditions of HPLC are as shown in the following Table.

TABLE 6

| Column: | YMC-Pack Pro C18 RS-303 (5 μm, 4.6 mm φ × 25 cm) (manufactured by YMC) |
|---|---|
| Eluent: | 50 mM ammonium formate |
| Flow rate: | 0.5 mL/minute |
| Retention time: | Shinorine: around 5 minutes Porphyra-334: around 7 minutes Mycosporine-glycine-alanine: around 9 minutes |

The UV absorption spectrum of a peak eluted around minutes had an absorption maximum at around 333 nm and exhibited the same pattern as in shinorine and porphyra-334. The peak was ionized by ESI (fragmentor voltage of 200.0 V) and the accurate mass was measured by a TOF detector. The value of m/z ([M+H])$^+$) was 317.1338 (calculated value for $C_{13}H_{21}N_2O_7^+$: 317.1349).

Example 3

3. Production of MAA using *Corynebacterium*

The present inventors produced MAAs by using *Corynebacterium glutamicum*.

3-1. Introduction of MAA Biosynthetic Enzyme Genes 3-1-1. Introduction of MAA biosynthetic enzyme genes into *Corynebacterium glutamicum*

As MAA biosynthetic enzyme genes, amir_4256 (SEQ ID NO: 1), amir_4257 (SEQ ID NO: 2), amir_4258 (SEQ ID NO: 3) and amir_4259 (SEQ ID NO: 4) genes derived from *Actinosynnema mirum* DSM43827 were used. These genes were ligated to a vector having pBL1 ori, under the control of a gapA promoter (see, Appl Microbiol Biotechnol (2008) 81: 291-301) to obtain a gene expression vector. *Corynebacterium glutamicum* ATCC13032 (NITE accession number: NBRC 12168, deposited with International Patent Organism Depositary (IPOD), National Institute of Technology and Evaluation (NITE), located at 2-5-8, Kazusakamatari, Kisarazu-shi, Chiba) was transformed with the gene expression vector by electroporation to obtain an MAA producing strain. The electroporation was carried out in accordance with a conventionally known method.

3-2. Pre-Culture of *Corynebacterium glutamicum*

To 50 mL of BHI culture medium (see Table 7), a glycerol stock of bacterium glutamicum ATCC13032 having the MAA biosynthetic enzyme genes, which was prepared in Section 3-1 above, was added. The *Corynebacterium glutamicum* was cultured at 30° C. and shaken at 180 rpm for 24 hours.

TABLE 7

| BHI medium | |
|---|---|
| Brain Heart infusion | 37 g |
| Total | 1000 mL |

3-3. Main Culture of *Corynebacterium glutamicum*

The pre-culture solution (an amount corresponding to 3%) was added to 50 mL of BHI culture medium contained in a Sakaguchi flask. At the starting of the culture, 5 mL of 400 g/L sodium gluconate was further added to the BHI culture medium such that the initial concentration of sodium gluconate became 20 g/L. To adjust pH, 5 mL of 10% calcium carbonate solution was added. The strain was cultured at 30° C. and shaken at 160 rpm for 48 hours.

3-4. Measurement of MAA

During the main culture, 1 mL of the culture solution was sampled at a predetermined time and the turbidity of the sampled culture solution was measured at 600 nm. The sampled culture solution was centrifuged at 15000 rpm for 10 minutes to separate extracellular culture solution and a precipitate (microbial cells). The separated extracellular culture solution was filtered by using a membrane filter having a pore diameter of 0.2 μm and the filtrate was used as an extracellular culture solution-sample. The production amounts of shinorine and porphyra-334 in the extracellular culture solution-sample were measured by HPLC. The Measurement conditions of HPLC are the same as shown in Table 5.

3-5. Results

Figure 2:
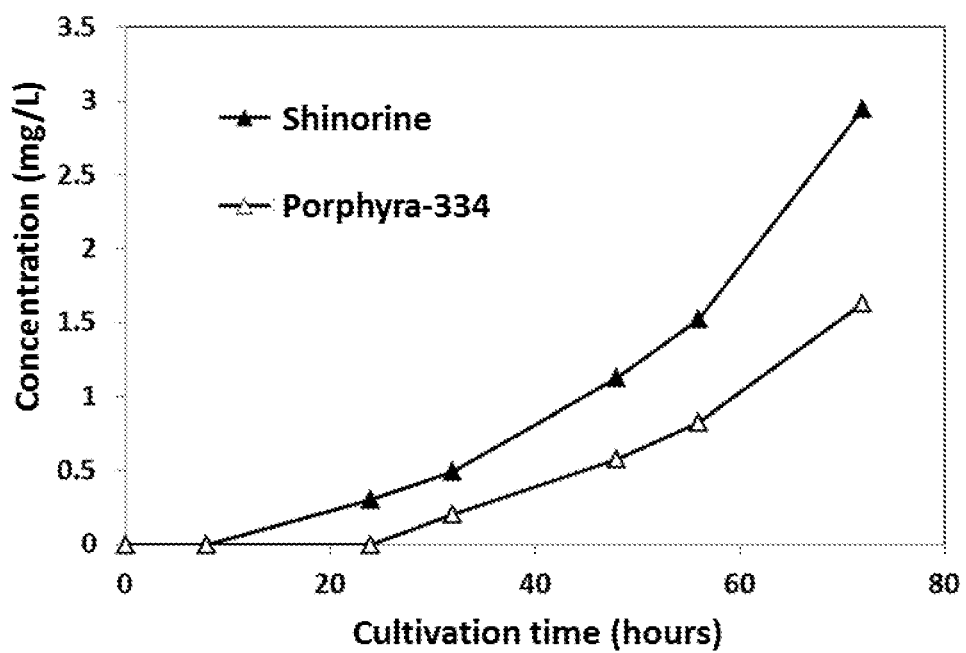
FIG. 2 shows temporal changes of the concentrations of shinorine and porphyra-334, in extracellular culture solution of *Corynebacterium glutamicum* ATCC13032 (NITE accession number: NBRC 12168). Black triangle: Shinorine; White triangle: Porphyra-334.

The results are shown in FIG. 2. It was verified that both shinorine and porphyra-34 are present in the extracellular culture solution.

Example 4

4. Production of MAA using Yeast

The present inventors produced MAAs by using *Saccharomyces cerevisiae*.

4-1. Introduction of MAA Biosynthetic Enzyme Genes 4-1-1. Construction of YPH499XW Cassettes separately expressing XYL1 (xylose reductase derived from *Scheffersomyces stipitis*)(SEQ ID NO: 13) XYL2 (xylitol dehydrogenase derived from *Scheffersomyces stipitis*)(SEQ ID NO: 14), and XKS1 (xylulokinase derived from *Saccharomyces cerevisiae*) (SEQ ID NO: 15) each encoding a xylose-assimilating gene, under the control of TDH3 promoter were digested with BssHII from plasmid pWX1X2XK (see, Appl Environ Microbiol. 2004 September 70 (9): 5407-14). These cassettes were ligated to pRS404 vector (ATCC accession number: ATCC 87515) digested with BssHII and having TRP1 selection marker to prepare a genomic integration vector pIWX1X2XK. The genomic integration vector pIWX1X2XK was treated with EcoRV. *Saccharomyces cerevisiae* YPH499 (Genetics 1969 May; 122 (1): 19-27) was transformed with the obtained fragments to obtain YPH499XW having xylose-assimilating ability. *Saccharomyces cerevisiae* was transformed in accordance with a conventionally known method.

4-1-2. Introduction of MAA Biosynthetic Enzyme Genes into *Saccharomyces cerevisiae* YPH499XW MAA biosynthetic enzyme genes, amir 4256 (SEQ ID NO: 1) and amir 4257 (SEQ ID NO: 2) were ligated to pAT426 vector (FEMS Yeast Res. 2014 May; 14 (3): 399-411) having 2μ ori and URA3 selection marker such that these genes were expressed under the control of TDH3 promoter and ADH1 promoter to prepare a gene expression vector pAT426-amir4256-7. Furthermore, MAA biosynthetic enzyme genes, amir4258 (SEQ ID NO: 3) and amir4259 (SEQ ID NO: 4) were ligated to pAT425 vector (FEMS Yeast Res. 2014 May; 14 (3): 399-411) having 2μ ori under the control of TDH3 promoter and ADH1 promoter to obtain a gene expression vector pAT425-amir4258-9. YPH499XW was transformed with these gene expression vectors pAT426-amir4256-7 and pAT425-amir4258-9 to obtain an MAA producing strain, i.e., YPH499XWMAA. *Saccharomyces cerevisiae* was transformed in accordance with a conventionally known method.

4-2. Pre-Culture of YPH499XWMAA

A glycerol stock of YPH499XWMAA having MAA biosynthetic enzyme genes, which was prepared in section 5-1 above, was cultured on SD-LUW agar medium (see, the following Table 8). Thereafter, the obtained colony was inoculated onto 5 mL of SX-LUW liquid medium (see, the following Table 9). The strain was cultured at 30° C. and shaken at 150 rpm for 13 days.

TABLE 8

SD-LUW agar medium

| | |
|---|---|
| Yeast Nitrogen Base w/o Amino Acids | 6.7 g (0.67%) |
| D-Glucose | 20 g (2%) |
| Adenine Sulfate | 40 mg (0.004%) |
| L-Histidine | 20 mg (0.002%) |
| L-Lysine | 30 mg (0.003%) |
| Agar powder | 20 g (2%) |
| Total | 1000 mL |

TABLE 9

SX-LUW liquid medium

| | |
|---|---|
| Yeast Nitrogen Base w/o Amino Acids | 6.7 g (0.67%) |
| D-Glucose | 20 g (2%) |
| Adenine Sulfate | 40 mg (0.004%) |
| L-Histidine | 20 mg (0.002%) |
| L-Lysine | 30 mg (0.003%) |
| Total | 1000 mL |

4-3. Main Culture of YPH499XWMAA

The pre-culture solution (an amount corresponding to 2%) was added to 100 mL of SD-LU liquid medium contained in a 300 mL baffled flask. The strain was cultured at 30° C. and shaken at 150 rpm for 48 hours.

4-4. Measurement of MAA

After culture was continued for 13 days, 4 mL of the culture solution was sampled and the turbidity of the sampled culture solution was measured at 600 nm. The sampled culture solution was centrifuged at 3,000 rpm for 5 minutes to separate extracellular culture solution and a precipitate (microbial cells). The separated extracellular culture solution was passed through a PTFE filter (0.45 μm) and the resultant solution was used as an extracellular culture solution-sample.

4-5. Results

The MAA concentration of the extracellular culture solution was measured. As a result, shinorine was extracellularly produced in an amount of 0.19 mg/L.

Example 5

5. Production of MAA using Labyrinthulea

The present inventors produced MAAs using labyrinthulea.

5-1. Introduction of MAA Biosynthetic Enzyme Genes
5-1. Introduction of MAA Biosynthetic Enzyme Genes into Labyrinthulea For *Aurantiochytrium* (*Aurantiochytrium* sp.) SAM2179 (FERM BP-5601), the codons the above genes, amir_4256 (SEQ ID NO: 1), amir_4257 (SEQ ID NO: 2), amir_4258 (SEQ ID NO: 3) and amir_4259 (SEQ ID NO: 4) were modified (SEQ ID NOs: 9 to 12,respectively), These genes thus modified were introduced into *Aurantiochytrium* SAM2179 by homologous recombination to obtain an MAA producing strain. Homologous recombination of the labyrinthulea was carried out in accordance with a conventionally known method.

5-2. Pre-Culture of *Aurantiochytrium*

To GY seawater medium plate containing 1.5% agar (see, the following Table 10), a glycerol stock of *Aurantiochytrium* SAM2179 having the MAA biosynthetic enzyme genes, which was prepared in Section 5-1 above, was added. The *Aurantiochytrium* was cultured at 28° C. for 2 days.

TABLE 10

GY seawater medium plate (pH 6.5)

| | |
|---|---|
| Glucose | 20 g (2%) |
| Yeast extract | 10 g (1%) |
| Daigo's artificial seawater | 18 g |
| Agar | 15 g |
| Total | 1000 mL |

5-3. Main Culture of *Aurantiochytrium*

*Aurantiochytrium* pre-cultured in Section 5-2 above was cultured in 10 mL of GY seawater medium (see, the following Table 11) at 28° C. and shaken at 300 rpm for 5 days.

TABLE 11

GY seawater medium (pH 6.5)

| | |
|---|---|
| Glucose | 20 g (2%) |
| Yeast extract | 10 g (1%) |
| Daigo's artificial seawater | 18 g |
| Total | 1000 mL |

5-4. Measurement of MAA

After completion of the main culture, the culture solution was centrifuged at 15000 rpm for 10 minutes to separate extracellular culture solution and a precipitate (microbial cells). The separated extracellular culture solution was passed through a membrane filter having a pore diameter of 0.2 μm and the resultant solution was used as an extracellular culture solution-sample. The production amount shinorine in the extracellular culture solution sample was measured by HPLC. The measurement conditions of HPLC are the same as shown in Table 5.

5-5. Results

Shinorine was extracellularly produced in an amount of 1.5 mg/L.

Example 6

6. Production of MAA using *Escherichia coli*

The present inventors produced MAAs using *Escherichia cell.*

6-1. Introduction of MAA Biosynthetic Enzyme Genes
6-1-1. Introduction of MAA Biosynthetic Enzyme Genes into *Escherichia coli*

As MAA biosynthetic enzyme genes, amir_4256 (SEQ ID NO: 1), amir_4257 (SEQ ID NO: 2), amir_4258 (SEQ ID NO: 3) and amir_4259 (SEQ ID NO: 4) were used. These genes were ligated to a vector pkk223-3 (GenBank No. M77749) having pBR322 ori under the control of tac promoter to prepare a gene expression vector. *Escherichia coli* JM109 (product code: 9052, manufactured by Takara Bio Inc.) was transformed with this gene expression vector to obtain an MAA producing strain. *Escherichia coil* was transformed in accordance with a conventionally known method.

6-2. Pre-Culture of *Escherichia coli*

To 5 mL of LB culture medium (see, the following Table 12), a glycerol stock of *Escherichia coli* JM109 having the MAA biosynthetic enzyme genes, which was prepared in Section 6-1 above, was added. The *Escherichia coli* was cultured at 37° C. and shaken at 160 rpm for 18 hours.

TABLE 12

| LB medium (pH 7.0) | |
| --- | --- |
| Sodium chloride | 10 g (1%) |
| Bactotryptone | 10 g (1%) |
| Yeast extract | 5 g (0.5%) |
| Total | 1000 mL |

6-3. Main Culture of *Escherichia coli*

The pre-culture solution (an amount corresponding to 2%) was inoculated to 50 mL of LB culture medium contained in a 500 mL, baffled flask. Sodium gluconate was further added to the LB culture medium at the starting of the culture such that the initial concentration of sodium gluconate became 50 g/L (a final concentration of 50 g/L), and calcium carbonate was further added such that its final concentration became 0.5%. The strain was cultured at 30° C. and shaken at 160 rpm a week.

6-4. Measurement of MAA

Twenty four hours after initiation of the main culture, 1 mL of the culture solution was sampled and centrifuged at 14000 rpm for 10 minutes to separate extracellular culture solution and a precipitate (microbial cells). The separated extracellular culture solution was used as an extracellular culture solution-sample. The production amount of shinorine in the extracellular culture solution-sample was measured by HPLC. The measurement conditions of HPLC are the same as shown in Table 5.

6-5. Results

The concentration of MAA in the extracellular culture solution was measured. As a result, shinorine was extracellularly produced in an amount of 0.82 mg/L.

From the foregoing, it was demonstrated that an MAA can be produced by using a microorganism and recovered from extracellular culture solution. In addition, it was demonstrated that a novel MAA, i.e., mycosporine-glycine-alanine, can be obtained. According to the method of the present invention, MAAs can be obtained from extracellular culture solution. This is extremely advantageous in relation to the subsequent purification process.

INDUSTRIAL APPLICABILITY

According to the method of the present invention, an MAA can be obtained stably in a large amount by use of a microorganism. The MAA obtained in this way can be used as an active ingredient of a UV-absorbing composition. Accordingly, the present invention can be used in the fields of e.g., cosmetics and pharmaceuticals.

Sequence Listing Free Text

SEQ ID NO: 9: Codon-optimized amir_4256 for SAM2179
SEQ ID NO: 10: Codon-optimized amir_4257 for SAM2179
SEQ TO NO: 11: Codon-optimized amir_4258 for SAM2179
SEQ ID NO: 12: Codon-optimized amir_4259 for SAM2179

The invention claimed is:

1. A method for producing a mycosporine-like amino acid in an extracellular culture solution, the method comprising:
culturing a microorganism that extracellularly produces a mycosporine-like amino acid, thereby producing the mycosporine-like amino acid in an extracellular culture solution,
separating the microorganism and the extracellular culture solution, and
recovering the mycosporine-like amino acid from the extracellular culture solution,
wherein the microorganism comprises heterologous nucleic acid encoding mycosporine-like amino acid biosynthetic enzymes,
wherein the heterologous nucleic acid encoding mycosporine-like amino acid biosynthetic enzymes comprises
a polynucleotide comprising the nucleotide sequence of SEQ ID NO: 1 or 9,
a polynucleotide comprising the nucleotide sequence of SEQ ID NO: 2 or 10,
a polynucleotide comprising the nucleotide sequence of SEQ ID NO: 3 or 11, and
a polynucleotide comprising the nucleotide sequence of SEQ ID NO: 4 or 12 and
wherein the mycosporine-like amino acid is at least one selected from the group consisting of shinorine, porphyra-334, and mycosporine-glycine-alanine.

2. The method according to claim 1, further comprising purifying the recovered mycosporine-like amino acid.

3. The method according to claim 1, wherein the microorganism is a microorganism selected from the group consisting of to *Escherichia coli*, yeast, actinomycetes, microalgae and labyrinthulea.

4. The method according to claim 3, wherein the microorganism is an actinomycete.

5. The method according to claim 4, wherein the actinomycete belongs to the genus *Streptomyces*, the genus *Actinosynnema*, the genus *Pseudonocardia* or the genus *Corynebacterium*.

6. The method according to claim 3, wherein the microorganism is labyrinthulea and belongs to the genus *Aurantiochytrium*.

7. The method according to claim 3, wherein the microorganism is yeast and belongs to the genus *Saccharomyces*.

8. A method for producing a mycosporine-like amino acid in an extracellular culture solution, the method comprising:
culturing a microorganism that extracellularly produces a mycosporine-like amino acid, thereby producing the mycosporine-like amino acid in an extracellular culture solution,
separating the microorganism and the extracellular culture solution, and
recovering the mycosporine-like amino acid from the extracellular culture solution,
wherein the microorganism comprises heterologous nucleic acid encoding mycosporine-like amino acid biosynthetic enzymes,
wherein the heterologous nucleic acid encoding mycosporine-like amino acid biosynthetic enzymes comprises a polynucleotide comprising the nucleotide sequence of SEQ ID NO: 1 or a codon-optimized sequence of SEQ ID NO: 1, wherein the codon-optimized sequence of SEQ ID NO: 1 encodes the same amino acid sequence encoded by the nucleotide sequence of SEQ ID NO: 1, a polynucleotide comprising the nucleotide sequence of SEQ ID NO: 2 or a codon-optimized sequence of SEQ ID NO: 2, wherein the codon-optimized sequence of SEQ ID NO: 2 encodes the same amino acid sequence encoded by the nucleotide sequence of SEQ ID NO: 2, a polynucleotide comprising the nucleotide sequence of SEQ ID NO: 3 or a codon-optimized sequence of SEQ ID NO: 3, wherein the codon-optimized sequence of SEQ ID NO: 3 encodes the same amino acid sequence encoded by the nucleotide sequence of SEQ ID NO: 3, and a polynucleotide comprising the nucleotide sequence of SEQ ID NO: 4 or a codon-optimized sequence of SEQ ID NO: 4, wherein the codon-optimized sequence of SEQ ID NO: 4 encodes the same amino acid sequence encoded by the nucleotide sequence of SEQ ID NO: 4, wherein codons of the codon-optimized sequences of SEQ ID NOs: 1-4 are optimized for expression in the microorganism, and wherein the mycosporine-like amino acid is at least one selected from the group consisting of shinorine, porphyra-334, and mycosporine-glycine-alanine.

9. The method according to claim 1, wherein the microorganism is *Streptomyces avermitilis* MA-4680, *Streptomyces lividans* 1326, *Corynebacterium glutamicum* ATCC13032, *Aurantiochytrium* sp. SAM2179, *Escherichia coli* JM109, or *Saccharomyces cerevisiae*.

10. The method according to claim 8, wherein the microorganism is *Streptomyces avermitilis* MA-4680, *Streptomyces lividans* 1326, *Corynebacterium glutamicum* ATCC13032, *Aurantiochytrium* sp. SAM2179, *Escherichia coli* JM109, or *Saccharomyces cerevisiae*.

* * * * *